(12) United States Patent
Kramer-Brown et al.

(10) Patent No.: US 9,265,866 B2
(45) Date of Patent: Feb. 23, 2016

(54) COMPOSITE POLYMERIC AND METALLIC STENT WITH RADIOPACITY

(75) Inventors: Pamela A. Kramer-Brown, San Jose, CA (US); David C. Gale, San Jose, CA (US); Vincent J. Gueriguian, San Francisco, CA (US); Yunbing Wang, Sunnyvale, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 1019 days.

(21) Appl. No.: 11/888,500

(22) Filed: Jul. 31, 2007

(65) Prior Publication Data

US 2008/0058919 A1 Mar. 6, 2008

Related U.S. Application Data

(60) Provisional application No. 60/834,887, filed on Aug. 1, 2006, provisional application No. 60/835,219, filed on Aug. 2, 2006.

(51) Int. Cl.
| | |
|---|---|
| *A61F 2/82* | (2013.01) |
| *A61L 31/18* | (2006.01) |
| *A61L 31/08* | (2006.01) |
| *A61L 31/12* | (2006.01) |
| *A61L 31/14* | (2006.01) |
| *A61L 31/16* | (2006.01) |
| *A61F 2/915* | (2013.01) |

(52) U.S. Cl.
CPC .......... *A61L 31/18* (2013.01); *A61L 31/08* (2013.01); *A61L 31/128* (2013.01); *A61L 31/148* (2013.01); *A61L 31/16* (2013.01); *A61F 2/82* (2013.01); *A61F 2/915* (2013.01); *A61F 2002/91558* (2013.01); *A61F 2002/91566* (2013.01); *A61F 2210/0004* (2013.01); *A61F 2250/0067* (2013.01); *A61F 2250/0096* (2013.01); *A61F 2250/0097* (2013.01); *A61L 2300/00* (2013.01); *A61L 2300/606* (2013.01)

(58) Field of Classification Search
USPC ........................................................ 623/1.34
See application file for complete search history.

(56) References Cited

U.S. PATENT DOCUMENTS

| | | |
|---|---|---|
| 4,405,319 A | 9/1983 | Cosentino |
| 4,458,366 A | 7/1984 | MacGregor |
| 5,078,736 A | 1/1992 | Behl |
| 5,171,262 A | 12/1992 | MacGregor |
| 5,477,864 A | 12/1995 | Davidson |
| 5,518,730 A | 5/1996 | Fuisz |

(Continued)

FOREIGN PATENT DOCUMENTS

| | | |
|---|---|---|
| DE | 198 56 983 A1 | 12/1999 |
| DE | 103 57 747 A1 | 1/2005 |

(Continued)

OTHER PUBLICATIONS

"Stent", The Free Online Medical Dictionary, accessed Jul. 10, 2013.*

(Continued)

*Primary Examiner* — Yashita Sharma
*Assistant Examiner* — Rebecca Preston
(74) *Attorney, Agent, or Firm* — Squire Patton Boggs (US) LLP

(57) ABSTRACT

Various embodiments of stents with a polymeric body with radiopaque metallic particles incorporated in the stent body.

23 Claims, 5 Drawing Sheets

(56) References Cited

U.S. PATENT DOCUMENTS

| | | | |
|---|---|---|---|
| 5,540,712 | A | 7/1996 | Kleshinski et al. |
| 5,624,411 | A | 4/1997 | Tuch |
| 5,637,113 | A | 6/1997 | Tartaglia et al. |
| 5,641,443 | A | 6/1997 | Calcote et al. |
| 5,769,884 | A | 6/1998 | Solovay |
| 5,843,172 | A | 12/1998 | Yan |
| 5,843,186 | A * | 12/1998 | Christ .......................... 623/6.56 |
| 5,873,904 | A | 2/1999 | Ragheb et al. |
| 5,916,584 | A | 6/1999 | O'Donoghue et al. |
| 5,972,027 | A | 10/1999 | Johnson |
| 6,174,329 | B1 | 1/2001 | Callol et al. |
| 6,241,719 | B1 | 6/2001 | Wallace et al. |
| 6,287,332 | B1 | 9/2001 | Bolz et al. |
| 6,287,484 | B1* | 9/2001 | Hausslein et al. ............ 252/512 |
| 6,355,058 | B1 | 3/2002 | Pacetti et al. |
| 6,585,755 | B2 | 7/2003 | Jackson et al. |
| 6,638,301 | B1 | 10/2003 | Chandrasekaran et al. |
| 6,702,850 | B1 | 3/2004 | Byun et al. |
| 6,730,120 | B2 | 5/2004 | Berg et al. |
| 6,736,842 | B2 | 5/2004 | Healy et al. |
| 6,867,248 | B1 | 3/2005 | Martin et al. |
| 6,926,733 | B2 | 8/2005 | Stinson |
| 7,011,678 | B2 | 3/2006 | Tenerz et al. |
| 7,241,856 | B2 | 7/2007 | Jin et al. |
| 7,476,889 | B2 | 1/2009 | DeMeo et al. |
| 7,951,194 | B2 | 5/2011 | Gueriguian |
| 8,172,897 | B2 | 5/2012 | Gale et al. |
| 2001/0029660 | A1 | 10/2001 | Johnson |
| 2002/0004060 | A1 | 1/2002 | Heublein et al. |
| 2002/0082679 | A1 | 6/2002 | Sirhan et al. |
| 2002/0165601 | A1 | 11/2002 | Clerc |
| 2003/0004563 | A1* | 1/2003 | Jackson et al. ............... 623/1.15 |
| 2003/0028241 | A1 | 2/2003 | Stinson |
| 2003/0065355 | A1 | 4/2003 | Weber |
| 2003/0083646 | A1 | 5/2003 | Sirhan et al. |
| 2003/0104028 | A1 | 6/2003 | Hossainy |
| 2003/0153972 | A1 | 8/2003 | Helmus |
| 2004/0008038 | A1 | 1/2004 | Morimoto |
| 2004/0034409 | A1 | 2/2004 | Heublein et al. |
| 2004/0088038 | A1 | 5/2004 | Dehnad et al. |
| 2004/0111149 | A1* | 6/2004 | Stinson ........................ 623/1.34 |
| 2004/0122509 | A1 | 6/2004 | Brodeur |
| 2005/0010275 | A1 | 1/2005 | Sahatjian et al. |
| 2005/0036946 | A1 | 2/2005 | Pathak et al. |
| 2005/0064223 | A1* | 3/2005 | Bavaro et al. ................. 428/615 |
| 2005/0064224 | A1 | 3/2005 | Bavaro et al. |
| 2005/0149173 | A1 | 7/2005 | Hunter et al. |
| 2005/0209680 | A1 | 9/2005 | Gale |
| 2005/0261760 | A1 | 11/2005 | Weber |
| 2005/0283229 | A1 | 12/2005 | Dugan et al. |
| 2006/0011103 | A1* | 1/2006 | Zhong ........................ 106/286.1 |
| 2006/0015053 | A1* | 1/2006 | Crisp .............................. 602/43 |
| 2006/0116752 | A1* | 6/2006 | Norton et al. ................. 623/1.34 |
| 2006/0229711 | A1 | 10/2006 | Yan et al. |
| 2006/0271168 | A1 | 11/2006 | Kleine et al. |
| 2007/0158880 | A1* | 7/2007 | Dave .............................. 264/635 |
| 2007/0200268 | A1* | 8/2007 | Dave .............................. 264/109 |
| 2008/0009939 | A1 | 1/2008 | Gueriguian et al. |
| 2008/0051866 | A1* | 2/2008 | Chen et al. .................... 623/1.11 |
| 2008/0319539 | A1 | 12/2008 | Gellman et al. |

FOREIGN PATENT DOCUMENTS

| | | |
|---|---|---|
| EP | 1 016 422 | 7/2000 |
| EP | 1 362 603 A2 | 11/2003 |
| EP | 2 026 854 B1 | 8/2010 |
| JP | 10-080492 | 3/1998 |
| JP | 2005538780 A | 12/2005 |
| JP | 2006501032 A | 1/2006 |
| JP | 2006511283 A | 4/2006 |
| WO | WO 98/18408 A1 | 5/1998 |
| WO | WO 98/56312 A1 | 12/1998 |
| WO | WO 99/03515 A2 | 1/1999 |
| WO | WO 01/04367 A1 | 1/2001 |
| WO | WO 03/026532 A2 | 4/2003 |
| WO | WO 03/063733 A1 | 8/2003 |
| WO | WO 2004/023985 A2 | 3/2004 |
| WO | WO 2004/030578 A2 | 4/2004 |
| WO | WO 2004/060210 A1 | 7/2004 |
| WO | WO 2006/108065 A2 | 10/2006 |
| WO | WO 2007/139668 A2 | 12/2007 |
| WO | WO 2008/016696 A2 | 2/2008 |

OTHER PUBLICATIONS

Davis, J.R., "Handbook of Materials for Medical Devices", 2003, ASM International, 3 pages (including front cover, first cover page, and p. 62), Accessed online Jul. 30, 2014.*

International Search Rep. for PCT/US2007/017289, filed Aug. 1, 2007, mailed Dec. 27, 2007, 6 pgs.

U.S. Appl. No. 11/799,354, filed Apr. 30, 2007, Wang et al.

U.S. Appl. No. 11/818,304, filed Jun. 13, 2007, Gale et al.

U.S. Appl. No. 11/968,600, file Jan. 2, 2008, Wang.

Barrett et al. "Endovascular Embolization of Varicoceles: Resorption of Tungsten Coils in the Spermatic Vein", Cardiovasc. Intervent. Radiol. 23, pp. 457-459 (2000).

Butler et al., "In vivo degradation of tungsten embolisation coils", The British J. of Radiology 73, pp. 601-603 (2000).

Peuster et al., "Degradation of tungsten coils implanted into the subclavian artery of New Zealand white rabbits is not associated with local or systemic toxicity", Biomaterials 24 pp. 393-399 (2003).

Wei Li "Dissolution of tungsten coils leads to device failure after transcatheter embolisation of pathologic vessels", Heart 85, pp. 703-704 (2001).

Weill et al., ""Corrosion" of Tungsten Spirals. A disturbing Finding", Interventional Neuroradiology 4 pp. 337-340 (1998).

European Search Rep. for Application 07836447.8 mailed Jun. 4, 2010, 5 pgs.

Coatings and anticorrosion protection, LaClusienne Clufix www.laclusienne.com, 10 pages.

Erli et al., Surface pretreatments for medical application of adhesion (2003) BioMedical Engineering OnLine 2:15, 18 pages.

Feng-Chun et al., Assessment of Tissue Blood Flow Following Small Artery Welding with an Intraluminal Dissolvable Stent (1999) *Microsurgery* 19:148-152.

Metals, alloys and metal compounds, Sciencelearn Hub, http://www.sciencelearn.org.nz/Contexts/Just-Elemental/Science-Ideas-and-Concepts/Meta..., published Oct. 25, 2009, printed Jul. 31, 2013, 3 pages.

Properties and Selection: Nonferrous Alloys and Special-Purpose Materials, taken from: Housh S., Mikucki B. ASM Handbook vol. 2, last updated Oct. 24, 2008 http://mg.tripod.com/asm_prop.htm.

Song et al., Electrodeposition of hydroxyapatite coating on AZ91D magnesium alloy for biomaterial application (2008) *Mat. Let.* 62:3276-3279.

Zhang et al., Processing and properties of porous poly(L-lactide)/bioactive glass composites (2004) *Biomaterials* 25:2489-2500.

Flinn et al., Engineering Materials and Their Applications, Second Edition, Corrosion of Metals: 12.7 Cell potentials in different solutions (1981) pp. 489-490; 4 pages total.

Galvanic corrosion, http://en.wikipedia.org/wiki/Galvanic_corrosion, printed Nov. 18, 2014, 9 pages.

* cited by examiner

COMPOSITE POLYMERIC AND METALLIC STENT WITH RADIOPACITY

CROSS REFERENCE TO RELATED APPLICATION

This application claims benefit of and incorporates by reference U.S. Patent Application No. 60/834,887, which was filed on 1 Aug. 2006, and U.S. Patent Application No. 60/835,219 which was filed on 2 Aug. 2006.

BACKGROUND OF THE INVENTION

1. Field of the Invention

This invention relates to stents, a type of implantable medical devices. In particular, the invention relates to polymeric stents containing radiopaque metallic particles.

2. Background

This invention relates to stents, which, among other uses, are used in the treatment of artherosclerosis. Atherosclerosis is a progressive disease which results in build-up of materials such as fats, cholesterol, calcium and cellular debris, the build-up collectively referred to as plaques, within the walls of arteries. The build-up of plaque along the artery walls results in hardening and constriction of the artery. When an artery that provides blood to the heart is clogged, resulting in a loss of blood flow or a severe reduction in blood flow to the heart, a heart attack results. A clot in an artery leading to the brain, potentially resulting from dislodged arterial plaque, results in a stroke. Coronary Artery Disease, the hardening and narrowing of arteries to the heart often resulting from artherosclerosis, is the leading cause of death in the United States for men and women.

This invention relates to radially expandable endoprostheses, which are adapted to be implanted in a bodily lumen. An "endoprosthesis" corresponds to an artificial device that is placed inside the body. A "lumen" refers to a cavity of a tubular organ such as a blood vessel. A stent is an example of such an endoprosthesis. Stents are generally cylindrically shaped devices, which function to hold open and sometimes expand a segment of a blood vessel or other anatomical lumen such as urinary tracts and bile ducts. Stents are often used in the treatment of atherosclerotic stenosis in blood vessels. "Stenosis" refers to a narrowing or constriction of the diameter of a bodily passage or orifice. In such treatments, stents reinforce body vessels and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

The structure of stents is typically composed of scaffolding that includes a pattern or network of interconnecting structural elements or struts. The scaffolding can be formed from wires, tubes, or sheets of material rolled into a cylindrical shape. In addition, a medicated stent may be fabricated by coating the surface of either a metallic or polymeric scaffolding with a polymeric carrier. The polymeric scaffolding may also serve as a carrier of an active agent or drug.

The first step in treatment of a diseased site with a stent is locating a region that may require treatment such as a suspected lesion in a vessel, typically by obtaining an x-ray image of the vessel. To obtain an image, a contrast agent, which contains a radiopaque substance such as iodine is injected into a vessel. "Radiopaque" refers to the ability of a substance to absorb x-rays. The x-ray image depicts the lumen of the vessel from which a physician can identify a potential treatment region. The treatment then involves both delivery and deployment of the stent. "Delivery" refers to introducing and transporting the stent through a bodily lumen to a region in a vessel that requires treatment. "Deployment" corresponds to the expanding of the stent within the lumen at the treatment region. Delivery and deployment of a stent are accomplished by positioning the stent about one end of a catheter, inserting the end of the catheter through the skin into a bodily lumen, advancing the catheter in the bodily lumen to a desired treatment location, expanding the stent at the treatment location, and removing the catheter from the lumen. In the case of a balloon expandable stent, the stent is mounted about a balloon disposed on the catheter. Mounting the stent typically involves compressing or crimping the stent onto the balloon. The stent is then expanded by inflating the balloon. The balloon may then be deflated and the catheter withdrawn. In the case of a self-expanding stent, the stent may be secured to the catheter via a retractable sheath or a sock. When the stent is in a desired bodily location, the sheath may be withdrawn allowing the stent to self-expand.

The stent must be able to simultaneously satisfy a number of mechanical requirements. First, the stent must be capable of withstanding the structural loads, namely radial compressive forces, imposed on the stent as it supports the walls of a vessel lumen. In addition to having adequate radial strength or more accurately, hoop strength, the stent should be longitudinally flexible to allow it to be maneuvered through a tortuous vascular path and to enable it to conform to a deployment site that may not be linear or may be subject to flexure. The material from which the stent is constructed must allow the stent to undergo expansion, which typically requires substantial deformation of localized portions of the stent's structure. Once expanded, the stent must maintain its size and shape throughout its service life despite the various forces that may come to bear thereon, including the cyclic loading induced by the beating heart. Finally, the stent must be biocompatible so as not to trigger any adverse vascular responses.

In addition to meeting the mechanical requirements described above, it is desirable for a stent to be radiopaque, or fluoroscopically visible under x-rays. Accurate stent placement is facilitated by real time visualization of the delivery of a stent. A cardiologist or interventional radiologist can track the delivery catheter through the patient's vasculature and precisely place the stent at the site of a lesion. This is typically accomplished by fluoroscopy or similar x-ray visualization procedures. For a stent to be fluoroscopically visible it must be more absorptive of x-rays than the surrounding tissue. Radiopaque materials in a stent may allow for its direct visualization.

In many treatment applications, the presence of a stent in a body may be necessary for a limited period of time until its intended function of, for example, maintaining vascular patency and/or drug delivery is accomplished. Therefore, stents fabricated from biodegradable, bioabsorbable, and/or bioerodable materials may be configured to meet this additional clinical requirement since they may be designed to completely erode after the clinical need for them has ended. Stents fabricated from biodegradable polymers are particularly promising, in part because they may be designed to completely erode within a desired time frame.

However, a significant shortcoming of biodegradable polymers (and polymers generally composed of carbon, hydrogen, oxygen, and nitrogen) is that they are radiolucent with no radiopacity. Biodegradable polymers tend to have x-ray absorption similar to body tissue.

SUMMARY

Some embodiments of the present invention are stents comprising a body comprising a polymer and radiopaque metallic particles mixed or dispersed within the body, wherein the body of the stent provides all of the structural support for the stent or substantially provides the structural support for the stent, and wherein the stent is visible in an X-ray image.

Further embodiments of the present invention are methods of manufacturing a stent, the method comprising mixing a polymer and metallic particles such that the metallic particles are mixed in, or dispersed in, the polymer, and then utilizing the resulting polymer/metallic particle mixture or dispersion to fabricate a stent, wherein the resulting stent is visible using X-ray imaging and the stent body provides all of the structural support for the stent or substantially provides the structural support for the stent.

Some embodiments of the present invention are stents comprising a body comprising poly(L-lactide) and radiopaque metallic particles mixed or dispersed within the body, and wherein the body of the stent provides the structural support or substantially provides the structural support for the stent, and wherein the metallic particles include Tungsten, at least one alloy comprising Tungsten, at least one oxide of Tungsten, at least one compound comprising Tungsten, Platinum, at least one alloy comprising Platinum, at least one oxide of Platinum, at least one compound comprising Platinum, or a combination thereof.

DETAILED DESCRIPTION OF THE INVENTION

Figure 1:
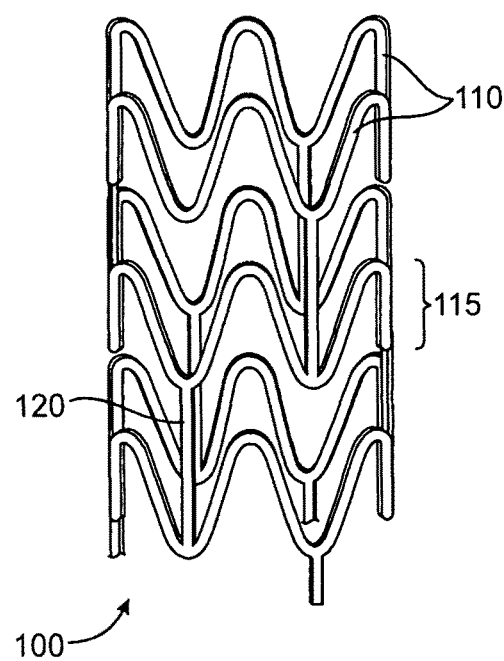
FIG. 1 depicts an exemplary stent.

In the discussion that follows, to avoid the stilted language required to consistently indicate that the plural of various aspects of this invention is included with the singular, any reference to the singular implies the plural and visa-versa, unless expressly stated to be otherwise; for example, "a bioactive agent" or "the bioactive agent" will refer to a single bioactive agent or to a plurality of bioactive agents; "a polymer" or "the polymer" will refer to a single polymer or a plurality of polymers; "the radiopaque metallic particles" will refer to a single species of radiopaque metallic particles or a plurality of species of radiopaque metallic particles, etc.

Terms such as "element", "member", "device", "section", "portion", "step", "means" and words of similar import when used herein shall not be construed as invoking the provisions of 35 U.S.C. .sctn. 112(6) unless the following claims expressly use the term "means" followed by a particular function without specific structure or the term "step" followed by a particular function without specific action.

Unless defined otherwise, all technical and scientific terms used herein have the same meaning as commonly understood by one of ordinary skill in the art to which the invention belongs.

For the purposes of the present invention, the following terms and definitions apply:

"Radiopaque" refers to the ability of a substance to absorb X-rays. Few substances will transmit 100% of X-rays and few substances will absorb 100% of X-rays. For the purposes of this disclosure, radiopaque will refer to those substances or materials which are capable of being imaged by an X-ray imaging device such as but not limited to a fluoroscope.

"Metallic particle" is a piece of matter held together by physical bonding of molecules, or a particle can also be an agglomeration of particles (e.g. pieces of matter held together by physical bonding of molecules) held together by colloidal forces, and/or surface forces. For the purposes of this disclosure, a particle will be defined as ranging in size from less than a one tenth of a nanometer to several centimeters in size. In addition, a particle may include one or more types of constituent molecules, and at least one of the constituent species or types of molecules is a metal, metal alloy, metal oxide, metallic salt, or other compound comprising a metal. Particle in this context does not refer to sub-atomic particles such as electrons, protons, neutrinos etc.

"Radiopaque metallic particle" as used herein is a metallic particle comprising a metal, provided that such metal is radiopaque, or a metal alloy, provided that such metal alloy is radiopaque, or an oxide and/or salt of metal, if such oxide and/or salt of metal is radiopaque, or another compound including a metal, provided that such compound is radiopaque, or any combination of the above.

"Contrast agent" is a material comprising a radiopaque substance such as, but not limited to, iodine.

"Radiopaque agent" is a material which is radiopaque, and this category includes radiopaque metallic particles, contrast agents, and other materials which are radiopaque.

"Patient" is an animal (an individual from a species included in the Kingdom animalia), including a human, in need of treatment for a disease, condition, treatment of symptoms of a disease or condition, or under medical care, or one who seeks treatment or medical care for a disease, condition or symptoms of a disease or condition.

"Composite" refers to "a combination of two or more materials each of which has its own distinctive properties" (Richard A. Flinn and Paul K. Trojan, *Engineering Materials and Their Applications*, $2^{nd}$ edition, Houghton Mifflin company, Boston, 1981).

"Comprising" means "including, but not limited to".

As used herein, unless specifically defined otherwise, any words of approximation such as without limitation, "about," "essentially," "substantially" and the like mean that the element so modified need not be exactly what is described but can vary from the description by as much as ±10% without exceeding the scope of this invention.

"Biocompatible" is "the ability of a material to perform with an appropriate host response in a specific application" (from D. F. Williams, "The Williams Dictionary of Biomaterials", c. 1999, ISBN 0-85323-921-5).

Overview

Various embodiments of the present invention may be applied to stents and, more generally, to implantable medical devices such as, but not limited to, self-expandable stents, balloon-expandable stents, stent-grafts, vascular grafts, or generally, tubular implantable medical devices. Other particular applications include temporary occlusive devices, pediatric applications, sealants, and grafts.

As outlined above, stents are used in the treatment of atherosclerotic stenosis in blood vessels. A stent can be used in the treatment or prevention of disorders such as, without limitation, thrombosis, restenosis, hemorrhage, vascular dissection or perforation, vascular aneurysm, chronic total occlusion, claudication, anastomotic proliferation, bile duct obstruction and ureter obstruction. In addition to the above uses, stents may also be employed for the localized delivery of therapeutic agents to specific treatment sites in a patient's body. In fact, active agent delivery may be the sole purpose of the stent or the stent may be primarily intended for another use such as those discussed above with drug delivery providing an ancillary benefit.

A stent can have virtually any structural pattern that is compatible with a bodily lumen in which it is implanted. Typically, a stent is composed of a pattern or network of circumferential and longitudinally extending interconnecting structural elements or struts. In general, the struts are arranged in patterns, which are designed to contact the lumen walls of a vessel and to maintain vascular patency. A myriad of strut patterns are known in the art for achieving particular design goals. A few of the more important design characteristics of stents are radial or hoop strength, expansion ratio or coverage area, and longitudinal flexibility. The present invention is applicable to virtually any stent design and is, therefore, not limited to any particular stent design or pattern. One embodiment of a stent pattern may include cylindrical rings composed of struts. The cylindrical rings may be connected by connecting struts.

The stent must be able to simultaneously satisfy a number of mechanical requirements. As noted above a stent must be delivered and deployed in a body lumen, and this is typically performed by mounting the stent to a delivery device such as but not limited to crimping the stent onto a catheter balloon. Thus, the stent must withstand the mechanical stress from crimping, or other mounting procedures. The stent should be longitudinally flexible to allow it to be maneuvered through a tortuous vascular path and to enable it to conform to a deployment site that may not be linear or may be subject to flexure. Due to the above mentioned need for deployment, the material from which the stent is constructed must allow the stent to undergo expansion, which typically requires substantial deformation of localized portions of the stent's structure. Once expanded, the stent must maintain its size and shape throughout its service life despite the various forces that may come to bear thereon, including the cyclic loading induced by the beating heart. In use, the stent must be capable of withstanding the structural loads, namely radial compressive forces, imposed on the stent as it supports the walls of a vessel lumen. This requires that the stent have adequate radial strength or more accurately, hoop strength. Finally, the stent must be biocompatible. As noted above, the present invention is not limited to any particular stent pattern or design.

There are numerous methods of manufacturing stents. In some embodiments, a stent of the present invention may be formed from a tube by laser cutting the pattern of struts in the tube. The stent may also be formed by laser cutting a polymeric sheet, rolling the pattern into the shape of the cylindrical stent, and providing a longitudinal weld to form the stent. Other methods of forming stents are well known and include chemically etching a polymeric sheet and rolling and then welding it to form the stent. Other means of manufacturing stents include, but are not limited to, using wire or fiber to fabricate a scaffold or coil. A stent may be fabricated from a woven material manufactured from, or including, wire and/or fibers. The various embodiments of the present invention are not limited to a particular stent design or structure, nor are the various embodiments of the present invention limited to any particular manufacturing techniques.

The structure of stents is typically composed of, but not limited to, scaffolding that includes a pattern or network of interconnecting structural elements or struts. An example of a stent is shown in FIG. 1. FIG. 1 depicts an exemplary stent 100 with struts 110 that form cylindrical rings 115 which are connected by linking struts 120. The cross-section of the struts in stent 100 is rectangular-shaped. The stent body may be the scaffolding of the stent such as that shown in FIG. 1. Some stents are helix shaped in design and in such a case the stent body would be the helix which supports a body lumen. The cross-section of struts is not limited to what has been illustrated, and therefore, other cross-sectional shapes are applicable with embodiments of the present invention. The stent and stent pattern illustrated in FIG. 1 is an example of the type of stent structure or stent pattern that may be used in the present invention but the present invention is in no way limited to the stent structure or stent pattern that is illustrated in FIG. 1. Other stent patterns are easily applicable with embodiments of the present invention.

In general, stents may be manufactured of metal, polymers, and/or other materials. The present invention relates to stents fabricated from, or including, polymers. As outlined above, it is desirable to be able to visualize the stent after deployment at a site in a body lumen. Although metal stents can be detected by X-ray visualization, as noted above, a significant shortcoming of biodegradable polymers (and polymers generally composed of carbon, hydrogen, oxygen, and nitrogen) is that they are radiolucent with no radiopacity. The extent of absorption is not significantly different from the absorption of the surrounding tissue with the result that polymers generally are not detected by X-rays. Thus, some embodiments of the current invention include a stent body formed from a polymer with radiopaque metallic particles mixed or dispersed within the polymer. The body of the stent provides most or all of the mechanical support for wall of a bodily lumen. Thus the thickness of the stent or the stent struts may be large enough that the stent has sufficient radial strength to support such bodily lumen. In addition, an entirely metal stent may be problematic in magnetic resonance imaging ("MRI") due to artifacts created which do not allow one to see around it. In contrast, it is expected that a polymer based stent including radiopaque metallic particles may be radiopaque enough to be detected yet allow visualization around the stent.

The present invention relates to various embodiments of stents manufactured from a polymer, metal, and optionally including other materials. The stents can be visualized by X-rays due to the incorporation of radiopaque metallic particles in the polymeric body of the stent. These stents may optionally be further coated and/or may further include an active agent. The radiopacity of the stent is due to the metallic particles incorporated in the polymer of which the stent body is fabricated as opposed to metallic particles or other material incorporated in a coating.

Radiopaque Metallic Particles

As noted above, the various embodiments of the present invention may be visualized by X-rays due to the incorporation of radiopaque metallic particles. Radiopaque materials, as defined herein, refers to those substances or materials which can be differentiated from the surrounding tissue of the patient in an X-ray image or fluoroscopic image. As a generalization, radiopaque materials are those materials that are not transparent to X-rays or other types of radiation; although the X-rays or radiation may not be entirely blocked (there may be some transmission of X-rays or other radiation). Materials with a high electron density interact more with X-rays. The higher atomic number materials have increased electron density. In general dense materials, such as most metals, are radiopaque.

X-rays are a form of electromagenetic radiation with enough energy to cause ionization, or loss of an outer shell electron. A common source of X-rays is tungsten. Within a tube, a cathode, or electrically heated filament, produces electrons which are accelerated by a high voltage to impact the anode target, which is often tungsten. The X-rays are released when the electrons interact with the target.

Two general categories of metals which may be well-suited for use in the various embodiments of the present invention include refractory metals, that is those with a high resistance to heat, wear, and corrosion, and precious metals, that is those with high economic value and often also generally less chemically active than other metals.

Tungsten (W) is particularly advantageous due to its high density and relatively high mass absorption coefficient. The intensity of transmitted X-rays is provided by the following equation: $I = I_0 \exp(-\mu x) = I_0 \exp(-\mu_m \rho x)$ where I represents the transmitted intensity of the X-ray beam, $I_0$ represents the incident or initial intensity of the X-ray beam, $\mu$ represents the linear absorption coefficient ($cm^{-1}$), x represents the thickness of the material through which the beam is transmitted, $\mu_m$ represents the mass absorption coefficient ($cm^2/g$), and $\rho$ represents the material's density (Donald R. Askeland, *The Science and Engineering of Materials*, c. 1984, Wadsworth, Belmont, Calif.). Thus, a lower intensity of the transmitted X-ray indicates that the material is more radiopaque per unit mass. Thus, as the density of a material increases, the transmitted intensity decreases and the material is more radiopaque. Similarly, a higher $\mu_m$ results in a lower intensity of the transmitted X-rays, and thus the material with a higher $\mu_m$ is more radiopaque.

More specifically, Tungsten has a density ($\rho$) of 19.3 $g/cm^3$ and a mass absorption coefficient ($\mu_m$) of 2.88 $cm^2/g$ for tungsten X-rays, but Iron has a density ($\rho$) of 7.87 $g/cm^3$ and a mass absorption coefficient ($\mu_m$) of 0.265 $cm^2/g$ for tungsten X-rays, and Molybedenum has a density ($\rho$) of 10.2 $g/cm^3$ and a mass absorption coefficient ($\mu_m$) of 0.265 $cm^2/g$ for tungsten X-rays (Askeland, supra). Although Lead (Pb) has a higher mass absorption coefficient ($\mu_m$) than Tungsten of 3.5 $cm^2/g$, the density ($\rho$) of Lead is 11.34 $g/cm^3$ density, which is lower than that of Tungsten (Askeland, supra). Therefore, smaller particle sizes and/or a smaller overall mass of Tungsten is required for a specified reduction in X-ray intensity, thus allowing the visualization of the implantable medical device at lower amounts of metal.

Tungsten possesses other desirable properties. Tungsten is bioabsorbable, but Tungsten has a slower erosion rate than some other metals, potentially allowing for a longer period of radiopacity. Furthermore, Tungsten has good mechanical properties. It has a high modulus and is a hard material, and therefore, resistant to deformation during the processing. In addition, the high mass absorption coefficient and density of Tungsten potentially allow for a lower total volume or mass of particles, and the smaller fraction of particles is expected to have a lower impact on mechanical properties of the stent body.

Platinum (Pt) is also particularly advantageous due to its biocompatibility. Platinum is also radiopaque and similar to Tungsten it is corrosion resistant allowing for a longer period of radiopacity. Platinum has an atomic weight higher than that of Tungsten, but lower than Lead.

As noted above, some embodiments of the current invention include a stent body including, or fabricated from, a polymer with radiopaque metallic particles mixed in, dispersed within, or otherwise incorporated within, the body of the stent. The stent body may be the scaffolding or structure which supports, or provides substantial support, to a body lumen. In some embodiments, the stent body may include multiple layers. In some embodiments, the stent body is the fully-fabricated device prior to the application of coatings.

In the various embodiments of the present invention, the radiopacity of the stent is due to the radiopaque metallic particles in the composite of the stent body as opposed to any radiopaque metallic particles or other radiopaque materials or contrast agents contained in a coating. For a blend or dispersion used to fabricate a stent, the blend or dispersion including both radiopaque metallic particles and a polymer, the weight percent of radiopaque metallic particles may be sufficient to allow for the stent to be visualized by means such as, but not limited to, X rays. Also, the weight percent of the radiopaque metallic particles in the mixture or dispersion which is used to fabricate the stent body may not be so high that the blend or dispersion cannot be processed, or so high that the mechanical properties of the material are significantly impacted.

It is believed that the high percentage of radiopaque metallic particles can be high enough to negatively impact mechanical properties of the stent. Such an impact may be due to the poor adhesion between the radiopaque metallic particles and the polymer matrix. Addition of fillers, particularly addition of materials with a higher modulus, is a well known method of improving the mechanical properties of polymers (Ferdinand Rodriguez, *Principles of Polymer Systems*, Taylor and Francis, Bristol Pa. 1996). In general, good adhesion between a continuous polymeric phase and a discrete radiopaque metallic phase in a composite material facilitates the improvement of the mechanical performance of the composite. It is also known that the mechanical properties are hot improved if there is poor bonding or adhesion between the filler and polymer (Rodriguez). Thus, it is expected that good bonding between the radiopaque metallic particles and the polymer matrix will eliminate or at least ameliorate the impact of the filler addition on the mechanical properties. For example, the negative impact of a radiopaque metallic phase on the strength, modulus and fracture toughness of a polymer can be reduced or eliminated by good adhesion between the polymer and metallic particles.

One way of improving the adhesion between the polymer and the metallic particles is by the addition of an adhesion promoter. Thus, it is expected that the inclusion of an adhesion promoter and/or a coupling agent will allow for higher levels of radiopaque metallic particles to be included in the body of the stent with a limited impact on the mechanical properties. The adhesion promoter may be applied to or incorporated within the radiopaque metallic particles prior to blending or dispersing in the polymer which will be used to fabricate the stent body. In some embodiments, the adhesion promoter will form a bond between the metallic particles (radiopaque or not) and the polymer that would lose strength when exposed to moisture, thus allowing for degradation of the medical device, or stent. For example, the coupling agent 3-aminopropyltrimethoxysilane would be expected to enhance the bond between metallic particles and bioabsorbable polymers, but it is expected that the bond formed would become less strong in the presence of moisture.

It is believed that the appropriate combination of radiopaque metallic particles and adhesion promoters may result in a medical device, such as a stent, with enhanced mechanical properties compared to a medical device lacking the radiopaque metallic particles. Thus, in some embodiments, the stent may have enhanced mechanical properties, such as mechanical strength, radial strength, or an increased modulus compared to a stent without the radiopaque particles. In some embodiments, the enhanced mechanical strength may allow for a thinner scaffold for the stent. In still other embodiments, the metallic particles may be added to enhance the mechanical strength, without consideration of the radiopacity of the stent, or without consideration of the impact of the metallic particles to impart radiopacity to the stent. Thus, in some embodiments, the composite of which the stent is formed may include metallic particles that are not radiopaque. In still other embodiments, the composite of which the stent is formed may include metallic particles that are optionally radiopaque at a level for which radiopacity of the stent is not achieved. In such embodiments for which the stent is not radiopaque, or substantially not radiopaque, the inclusion of metallic particles, whether radiopaque or otherwise, may be for the purpose of increasing mechanical strength of the stent or medical device.

As outlined above the stent must satisfy a number of mechanical requirements, so the percent of radiopaque metallic particles may be limited due to the potential impact of the radiopaque metallic particles on a given mechanical property. Thus the weight percent of radiopaque particles dispersed within, or mixed in, the body of the stent may be optimized taking into account the need for radiopacity, the time frame for radiopacity, and any potential impact that the radiopaque metallic particles may have on the strength of the stent. The overall thickness and/or shape of the stent is also a consideration in determining the percentage of radiopaque metallic particles as a thicker stent or stent strut will be more radiopaque at a given weight percent of radiopaque metallic particles than a thinner stent or stent strut. As noted earlier, the intensity of transmitted X-rays is $I=I_0 exp(-\mu x)=I_0 exp(-\mu_m \rho x)$ where I represents the transmitted intensity of the X-ray beam, $I_0$ represents the incident or initial intensity of the X-ray beam, $\mu$ represents the linear absorption coefficient ($cm^{-1}$), x represents the thickness of the material through which the beam is transmitted, $\mu_m$ represents the mass absorption coefficient ($cm^2/g$), and $\rho$ represents the material's density. Thus, as the thickness of a particular material increases, the transmitted intensity decreases, and the result is that the material is more easily visualized with X-rays. Additionally, in those cases in which metallic particles, whether radiopaque or not, are added to increase mechanical strength, the increase in mechanical properties, optionally considered in conjunction with other stent properties, may be the major determinant of the level of metallic particles included in the composite from which the stent is formed.

The particular design of the stent will also impact the requirements for mechanical strength or other mechanical properties, as well as the impacting the percentage of radiopaque metallic particles needed to obtain a desired radiopacity. In some embodiments, the stent body is comprised of polymer and radiopaque metallic particles mixed in or dispersed in the body wherein the volume percent radiopaque metallic particles is from about 2% to about 36%. Preferably, the volume percent of the radiopaque metallic particles in the stent body is from about 5% to about 30%, and more preferably between about 5% and 20%. For the purposes of this disclosure, the volume percent metallic particles are determined by the volume percent metallic particles in the stent body, prior to any optional coating.

In some embodiments of the present invention, the radiopaque metallic particles mixed or dispersed in the body of the stent may be biostable. In other embodiments, the radiopaque metallic particles may be bioerodible. In still other embodiments, the radiopaque metallic particles may include both biostable metals and bioerodible metals. In yet other embodiments, a combination of at least one species of biostable radiopaque metallic particles and at least one species of bioerodible radiopaque metallic particles may be utilized.

Some metals are considered bioerodible since they tend to erode or corrode relatively rapidly when exposed to bodily fluids. Biostable metals refer to metals that are not bioerodible. Biostable metals have negligible erosion or corrosion rates when exposed to bodily fluids. In general, metal erosion or corrosion involves a chemical reaction between a metal surface and its environment. Erosion or corrosion in a wet environment, such as a vascular environment, results in removal of metal atoms from the metal surface. The metal atoms at the surface lose electrons and become actively charged ions that leave the metal to form salts in solution. Therefore, an erodible metal is one that has the propensity for self-dissolution in an in vivo environment, and a metal that undergoes self-dissolution in an in vivo environment corrodes when subjected to bodily fluids and breaks down. Representative examples of biodegradable, or bioerodible, metals may include, but are not limited to Tungsten, Magnesium, Zinc, and Iron. A metal suitable for use as a stent material will be chosen such that the metal, and any corrosion products of the metal if it is bioerodible, has little or no ill effect on the patient.

In some embodiments, the radiopaque metallic particles may include a metal that is typically considered to be biostable, but the particle size allows for absorption by the body. Particles that are sufficiently small may be opsinized, that is engulfed by macrophages and absorbed into the body. To ensure that the particles will be opsinized, particles should be smaller than about 7 to 10 $\mu m$.

In some embodiments, biostable radiopaque metallic particles may be included with a biodegradable polymer. In such embodiments, the stent body may degrade or erode over time, but leave behind the biostable radiopaque metallic particles. The remaining biostable radiopaque metallic particles may serve as a "marker" in the vessel or other lumen of the patient (or subject if a clinical or experimental study) to allow a physician to detect the prior location of the stent. Such markers may allow for a second stenting deployment at the site, and/or may allow the physician to better track or visualize the healing, or lack thereof, of the lesion.

In some embodiments, the radiopaque metallic particles may include oxides of biostable or bioerodible metals, while in other embodiments, the radiopaque metallic particles may include a biocompatible metallic salt. A biocompatible metallic salt refers to a salt that may be safely absorbed by a body. Representative biocompatible metallic salts that may used include, but are not limited to, Ferrous Sulfate, Ferrous Gluconate, Ferrous Carbonate, Ferrous Chloride, Ferrous Fumarate, Ferrous Iodide, Ferrous Lactate, Ferrous Succinate, Barium Sulfate, Bismuth Subcarbonate, Bismuth Potassium Tartrate, Bismuth Sodium Iodide, Bismuth Sodium Tartrate, Bismuth Sodium Triglycollamate, Bismuth Subsalicylate, Zinc Acetate, Zinc Carbonate, Zinc Citrate, Zinc Iodate, Zinc Iodide, Zinc Lactate, Zinc Phosphate, Zinc Salicylate, Zinc Stearate, Zinc Sulfate, and combinations thereof.

For bioerodible, or corridible metallic particles, whether radiopaque or not, a galvanic couple may be utilized. In some embodiments, the radiopaque metallic particles may include a combination of two or more metals selected to create a galvanic couple such that the material will undergo galvanic dissolution upon contact with bodily fluids. Reliance on galvanic corrosion in order to achieve a desired corrosion rate requires the selection of a metal pair that has a sufficiently high rest potential differential. A rest potential differential results from two metals that, by themselves, each have a particular rest potential when measured versus a reference electrode, for example a Standard Calomel Electrode (SCE) or Natural Hydrogen Electrode (NHE), in the same type of solution, for example saline or equine horse serum. The driving force toward corrosion that results from this differential may be tailored to control the rate of degradation of the joined materials. For example, a driving force of about 500 mV would generally result in a slower dissolution than a driving force of 1 V or more. Appropriate metal pairs can be selected from among, but not limited to, the elements Magnesium (Mg), Manganese (Mn), Potassium (K), Calcium (Ca), Sodium (Na), Zinc (Zn), Chromium (Cr), Iron (Fe), Cadmium (Cd), Aluminum (Al), Cobalt (Co), Antimony (Sb), Vanadium (V), Copper (Cu), Molybdenum (Mo), Tungsten (W), and from alloys based on such elements.

In one embodiment, bimetallic couples are extruded in a polymer. By co-extruding wire in a polymer, wire may be a spiral shape, a ring shape, or a criss-cross shape, or other shape. Multiple metal powders, galvanic couples, multiple wires or "pieces" of any shape and/or size of the metal may be used. In one embodiment, the metal particles may range in size up to 20 microns with an average particle size of three to four microns. The medical device can also include other materials besides polymer and metal, such as ceramic particles.

In some embodiments, the radiopaque metallic particles may include both biostable or bioerodible metals, and/or the radiopaque metallic particles may include a plurality of different types or species of radiopaque metallic particles. The radiopaque metallic particles may include one or more metals in any of the various forms including the metal, and/or metal oxides, metal salts and/or combinations of metals or metal alloys forming a galvanic couple. Other compounds including a metal may also be utilized provided that the metal is sufficient, at the weight percent of particles utilized, to provide the required radiopacity to the stent.

In some embodiments, the size of the radiopaque metallic particles may be small enough to reduce or eliminate the risk of thrombosis due to release of such particles from the body of the stent. Thrombosis is a clot formed in a blood vessel. In particular, reducing the size of the radiopaque metallic particles, if the composition is bioabsorbable, decreases their absorption time. In some embodiments, a dimension of the radiopaque metallic particles can be 10-100 µm, 100-200 µm, or greater than 200 µm. In some embodiments, to prevent the radiopaque metallic particles from being engulfed by macrophages, the particle size may be greater than about 20 µm. In still other embodiments, to increase absorption of radiopaque metallic particles, the particle size should be in the range from submicron up to about 20 µm.

In certain embodiments, the radiopaque metallic particles can be less than 10 µm. In particular, the particles can be nano-particles. A "nano-particle" refers to a particle with a dimension in the range of about 1 nm to about 500 nm. Another significant advantage of smaller particles, such as nano-particles, over larger particles is that nano-particles may disperse more uniformly in a polymeric, matrix, which results in more uniform radiopacity. In addition, it has been shown that the fracture toughness of a polymeric material can be improved by using nano-particles as a discrete or reinforcing phase in a composite. *J. of Applied Polymer Science,* 94 (2004) 796-802. It has been reported that composites with nano-particles can increase the modulus of a polymer by 1-2 orders of magnitude (*Mechanical Properties of Polymers and Composites,* Lawrence E. Nielsen and Robert F. Landel, $2^{nd}$ ed., p. 384-385 (1993)). In addition, the particles may act as a "cross-link" that can reduce or inhibit movement of polymer chains in amorphous regions of a polymer which may reduce or eliminate creep, stress relaxation, and physical aging.

In some embodiments of the present invention, the radiopaque metallic particles utilized may include several different sizes, or a range of sizes. These radiopaque metallic particles may all be of the same type or species of metallic particle or of different types or species. A type, or species, of metallic particle refers to a particular composition of the metallic particle. The types, or species, of metallic particles may differ in the type of the radiopaque metal used, the form of the radiopaque metal used, that is whether the metal is used or an oxide, salt or other compound of the metal is used, and whether or not other compounds are included in the particle, and if so, the type(s) of other chemical compound(s) included. In some embodiments, different sizes of radiopaque metallic particles will be used in different sections of the stent.

Depending upon the degree of radiopacity of radiopaque particles, the choice of particle size may be important. Although smaller particles will generally allow for a more uniform distribution, slightly larger sizes may be desirable in some embodiments. The use of larger average particle sizes results in greater spacing between filler particles at a given percentage, thus maintaining processability during compounding. Thus, in some embodiments, particularly for embodiments with high volume percent of radiopaque metallic particles, a particle size distribution having an average particle size range of at least 2 microns to 10 microns and a maximum particle size of about 20 microns may be utilized. Thus, the choice of particle size distribution will depend upon the particular embodiment.

The shape of the radiopaque metallic particles, or metallic particles, can vary. In some embodiments, the particles may be spherical, or substantially spherical. In some embodiments, the particles may be disk-shaped, round, or irregularly shaped. In some embodiments, the radiopaque metallic particles, or in some embodiments, metallic particles may be shaped like drawn and chopped fibers. In some embodiments, discrete particles of equiaxed shape may be used. It is believed that individual particles of irregular shape, including agglomerations of multiple particles, may adversely impact the surface. Thus, if a thin strut of a stent is desirable, some embodiments may include particles of similar shape or equiaxed shape.

It is believed that the process by which certain metal powders are produced has a profound effect on the shape of the individual particles. In the case of metallic Tungsten, the powders may be formed by the reduction of powdered oxides through either "rotary," "pusher" or "atomization" processing. Of these processes, "rotary" processing has been found to yield the least desirable shape and size distribution as partial sintering causes coarse agglomerates to be formed which do not break up during compounding or extrusion. Atomized powders have been reprocessed by melting and resolidifying "rotary" or "pusher" processed powders and results in generally equiaxed, discrete particles. If uniform shape is desirable, "pusher" processed powders are preferred due to their low cost and discrete, uniformly shaped particles.

In some embodiments the radiopaque metallic particles are uniformly, or essentially uniformly, distributed throughout the polymer body. In other embodiments the radiopaque metallic particles are distributed in a non-uniform manner throughout the polymer body. In some embodiments, the radiopaque metallic particles may be distributed with a preferentially higher concentration on the luminal side of the stent. In other embodiments the radiopaque metallic particles agent may be distributed with a preferentially higher concentration exists along the abluminal side of the stent. In some embodiments, the radiopaque metallic particles may be distributed in some other non-uniform manner.

Polymers

In some embodiments the polymer of the stent body may be a biostable polymer, a bioabsorbable polymer, or both. In general, polymers can be biostable, bioabsorbable, biodegradable, bioerodible, dissolvable, or water soluble. Biostable refers to polymers that are not bioabsorbable. The terms biodegradable, bioabsorbable, bioerodible, and biosoluble, as well as degraded, eroded, absorbed, and dissolved refer to polymers that are capable of being completely eroded or absorbed when exposed to bodily fluids such as blood and can be gradually resorbed, absorbed and/or eliminated by the body. In some embodiments utilizing a bioabsorbable polymer, very negligible traces or residue may be left behind.

Some bioabsorbable polymers absorb due to chemical degradation that occurs in a polymer upon exposure to bodily fluids as in a vascular environment. Chemical degradation refers to degradation of a polymer due to chemical reaction of the polymer with bodily fluids or substances within bodily fluids. The chemical degradation can result in a decrease in molecular weight, deterioration of mechanical properties, and decrease in mass due to erosion. Mechanical properties may correspond to strength and modulus of the polymer. Deterioration of the mechanical properties of the polymer decreases the ability of a stent, for example, to provide mechanical support in a vessel. The chemical degradation can be the result of hydrolysis, oxidation, enzymolysis, and/or metabolic processes. Additionally, some bioabsorbable polymers are water soluble. A water soluble polymer corresponds to a polymer that is capable of dissolving in water in addition to, or even in the absence of chemical degradation of the polymer.

Furthermore, polymer erosion spans a continuum from bulk eroding to surface eroding. Bulk eroding refers to degradation of a polymer throughout the bulk of a polymer part exposed to bodily fluids. Alternatively, a polymer may be surface eroding. A surface eroding polymer typically has relatively low water diffusivity. As a result, surface erosion is a heterogeneous process in which degradation and erosion tend to occur at or near a surface of the polymer exposed to the bodily fluids. The time frame of the degradation of various properties depends on such properties as the diffusivity of water in the polymer, and whether the polymer is bulk eroding, or surface eroding.

In some embodiments, the bioabsorbable polymer may be a water soluble polymer. Examples include, but are not limited to, poly(vinyl alcohol) (PVA) and poly(ethylene glycol) (PEG).

As outlined above, the use of "a polymer," or "the polymer" with respect to embodiments of the invention includes not only a single polymer, but a plurality of polymers, meaning more than one type of polymer. Encompassed in the terms "a polymer" and "the polymer" are various combinations of polymers, including, but not limited to, combinations of polymers that differ in chemical composition. In addition, the combination of polymers encompasses a combination of polymers of the same chemical composition, or essentially the same chemical composition, but differing in molecular weight (generally expressed as some average for polymers), molecular weight distribution, crystallinity, and/or tacticity, or some other variation. Combinations of polymers also encompasses combinations of polymers that may have the same or a similar chemical composition but differ because one is random copolymer and the other block copolymer, or one is a graft copolymer. Combinations of polymers also encompasses branched polymer versus linear polymer, polymers which vary by the degree of branching, uncross-linked polymer versus cross-linked, and/or polymers which vary by the degree of cross linking. Combinations of polymers also encompasses polymers of the same or essentially the same chemical composition but which vary in number, distribution, and/or type of substituents along a polymer backbone. Various combinations of any of the aforementioned variations in polymers are encompassed within the scope of the invention.

In some embodiments, the entire stent body can be bioabsorbable. In some embodiments the polymer may be bioabsorbable, while in other embodiments both the polymer is bioabsorbable and the radiopaque metallic particles are bioerodible. The "degradation time" for the stent, or stent body, is the time to completion of the processes of degradation, erosion, absorption, dissolution, and/or resorption. At the time of complete degradation either no portion of the bioabsorbable stent, or no part of the bioabsorbable portion of the stent, remains, or very negligible traces or residue of the stent, remains. The rate of biodegradation may be controlled by the choice of polymer of the body of the stent as well as the type and weight percent of the radiopaque metallic particles. As noted above, the choice of slow eroding, fast eroding, and water soluble polymers, and/or combinations thereof will allow for variation in the overall biodegradation rate of the stent. For those embodiments in which the polymer erodes, the radiopaque metallic particles may be released as the bioabsorbable polymer erodes. As outlined above, the radiopaque metallic particles can be erodible or nonerodible. Alternatively, the radiopaque metallic particles may erode prior to the erosion of the stent body so few or no particles are released upon degradation of the polymer of which the stent body is fabricated.

The bioerodible particles can erode prior to release from the stent body due to bulk erosion of the polymer. In general, erodible radiopaque metallic particles will have a lifetime that is shorter than the polymer. The erodible radiopaque metallic particles will erode as a result of diffusion of moisture into the polymer matrix. Erosion of the radiopaque metallic particles increases the equilibrium concentration of moisture in the body which increases the rate of degradation of the polymer. Thus, inclusion of radiopaque metallic particles may decrease the degradation time for the stent body. The use of the erosion of the radiopaque metallic particles is particularly useful for some crystalline or semi-crystalline polymers that are glassy or have a glass transition temperature (Tg) above body temperature. These polymers are particularly attractive as stent materials due to their strength and stiffness at physiological conditions. Such glassy polymers can be non-water soluble, but can be absorbed through chemical degradation, such as hydrolysis. However, these crystalline or semi-crystalline polymers that are glassy or have a glass transition temperature (Tg) above body temperature (about 37° C. for humans) have a relatively low degradation rate. Thus, the ratio of radiopaque metallic particles to the polymer may be used to control the erosion rate of the stent body.

Since a polymer and radiopaque metallic particles may have different erosion rates, the ratio of polymer to radiopaque metallic particles may be modified to obtain a desired erosion rate. The biodegradation time for the stent can also be controlled by altering the ratio of polymer and radiopaque metallic particles. For example, if a bioerodible metal has a faster erosion rate than the biodegradable polymer, decreasing the ratio of polymer to radiopaque metallic particles may increase the erosion rate of a device. Another variable that may be utilized in adjusting the erosion rate of the stent is the size of the bioerodible radiopaque metallic particles as the size of the particles decreases, the rate of degradation increases as a result of the higher surface area. Additional additives, not classified as either a polymer or a radiopaque metallic particle, may also impact the rate of erosion, and may be used to adjust the erosion rate.

In particular, for those embodiments in which the radiopaque metallic particles include a galvanic couple, the choice of the galvanic couple may influence the degradation rate. The degradation rate may be tailored by selecting a combination of metals that have a driving force of about 500 mV or greater. In one embodiment the driving force would be about 1 V or greater. For example, Ti has a rest potential of 3.5 V vs. SCE in equine serum, and would, when paired with almost any other metal, yield a suitable driving force. Alternatively, the pairings Nb—Cr (1.1 V rest potential differential vs. SCE in equine serum), Pd—W (1.23 V rest potential vs. SCE in equine serum), Cr—W (630 mV rest potential differential vs. SCE in equine serum), and Ir—Zn (830 mV rest potential differential vs. SCE in equine serum) would also yield suitable driving forces.

Another factor influencing the dissolution rate of the metallic particles is the porosity or surface area of the particles. By selecting the metal and the degree of porosity, the rates of degradation can be tailored to a range of applications. If the radiopaque metallic particles are manufactured from a microcellular porous metal, the morphology of the microcellular porous metal, including the cell size and porosity of the metal, can be controlled. The desired porosity is achievable by a variety of techniques including, but not limited to sintering, foaming, extrusion, thixomolding, semi-solid slurry casting and thermal spraying. However, consideration of the impact that a porous radiopaque metallic particles has on radiopacity is another consideration in the choice of the type and level of metallic particles along with the impact on the erosion rate of the device as a whole.

In some embodiments, the stent design and/or stent thickness may also be considered, as a factor in determining the erosion time. The stent pattern and design may also impact the time for erosion (complete erosion, or substantially complete erosion such as 85% to 90% or more). Thus in some embodiments, a change in the stent pattern or use of a different stent pattern may be used to adjust the degradation time or degradation rate.

Thus the stent may designed to be completely eroded, or substantially completely eroded (85% to 90% or more), in less than a month, between a month and three months, between three months and six months, between six months and a year, or greater than 1 year. As noted earlier, in some embodiments utilizing a bioabsorbable polymer, very negligible traces or residue may be left behind.

In some embodiments, the duration of the stent's useful lifetime may be designed to be about the same as or some time period longer than the duration time needed for treatment. In some embodiments, the stent's useful life time will be the same as or for some time period longer than the duration of active agent release where stent includes an active agent either in the body of the stent, or as a stent coating, or as a component of a stent coating. The useful lifetime of the stent is the time frame during which the stent performs its intended function such as providing mechanical support to the wall of a bodily lumen. Thus, if the stent degrades over time, at some point the mechanical properties or other properties may be impacted to such an extent that the stent no longer performs its intended function, such as, but not limited to, providing sufficient support to a bodily lumen. This point would define the end of the useful life of the stent.

As noted above, various embodiments may be used to obtain a desired erosion time by varying the types of and ratios of materials as well as the stent design. All such variations are considered to be within the scope of the invention.

Visualization of the Medical Device

In some embodiments, the required degradation time of a stent body and the time for visualization of a stent may be different. As noted previously, the visualization of the device is primarily due to the radiopaque metallic particles in the body of the stent and not to any materials in a coating applied to the device. In some embodiments, the stent may degrade over a particular time period and the stent may be visualized for all, or substantially all (90% or more), of the useful lifetime of the stent. In other embodiments, the stent may degrade a particular time period and the stent may be visualized for about 80% of the useful life-time of the stent, or for about 50% or 60% of the useful life-time of the stent.

In some embodiments, the stent body may include a polymer and the radiopaque metallic particles may be erodible so the time frame for visualization may be much shorter than the time frame of the stent's useful life. In some embodiments, the stent body may include a polymer and the radiopaque metallic particles may be bioerodible so the time frame for visualization will be much shorter than the time frame during which the stent remains implanted. In some embodiments, the time frame for visualization may be only shortly after implantation such as several hours, a day or a week after implantation, regardless of the time frame anticipated for the useful life of the stent. Thus, in some embodiments the stent may degrade over a year, but the time frame for visualization of the stent may be one day, one week, one month, or six months.

The time frame for visualization is a function of the degradation rate of the erodible radiopaque metallic particles and the degradation rate of the polymer of the stent body. If the radiopaque metallic particles are nonerodible, the non-erodible polymers leave the stent as the polymer of the stent body erodes and as a result the radiopacity of the stent decreases as fewer radiopaque particles remain in the stent. If the radiopaque metallic particles erode more quickly than the polymer of the stent body, the time frame for visualization will be largely determined by the erosion rate of the radiopaque metallic particles.

Optional Active Agent

In some embodiments, the stent may also include an active agent. The active agent may be incorporated into the body of the stent. In some embodiments, the active agent may be included in a microcapsule. The microcapsules or pellets including the active agent ("microcapsules") may release the drug when the coating is bioabsorbed or resorbed, and/or by diffusion of the active agent through the coating. In some embodiments the active agent and/or microcapsules may be uniformly or essentially uniformly distributed throughout the stent body, while in other embodiments, the distribution of the active agent and/or microcapsules is not uniform. In some embodiments, the active agent or microcapsules may be present at a higher concentration at or near the exterior surface of the stent, while in other embodiments, the active agent and/or microcapsules may be present at a higher concentration in the interior of the stent. In some embodiments, the active agent and/or microcapsules may be distributed with a preferentially higher concentration on the luminal side of the stent. In some embodiments, the active agent and/or microcapsules may be distributed with a preferentially higher concentration on the abluminal side of the stent. In other embodiments, the active agent and/or microcapsules may be distributed in some other non-uniform manner.

In other embodiments, the active agent may be coated on the exterior surface of the stent where the active agent is coated onto the stent by techniques known in the art. In the following paragraph, active agent will refer to active agent and/or microcapsules of active agent. In other embodiments, the coating may contain only the active agent, or essentially only the active agent. In other embodiments, the coating may include the active agent, dispersed within a polymer carrier, and optionally other carriers, binders, fillers or other additives. In some embodiments, coating of the exterior of the stent may be a coating of the entire exterior surface, while in other embodiments, some portions of the exterior surface may remain uncoated. In some embodiments, the coating may be applied to only a particular portion of the stent such as, but not limited to, a central axial section of the cylindrical device, or one or both ends. In some embodiments, only the abluminal side of the stent will be coated, and the luminal side is free of coating, or substantially free of coating (90% or more is free of coating). In some embodiments, only the luminal side of the stent may be coated, and the abluminal side is free of coating or substantially free of coating (90% or more is free of coating). If a polymer is used in the coating, the polymers that may be used in the coating include, but are not limited to, all of the polymers listed above for potential use in the stent body.

For the above embodiments in which the active agent is incorporated into the stent body or a coating include the active agent, the active agent may be released by diffusion from or diffusion through the stent or the stent coating. The active agent may also be released by degradation and/or dissolution of the stent, or the stent coating. Other potential mechanisms of active agent release include the degradation and/or dissolution of components of the stent, or of the stent coating, resulting in release of the active agent into the body fluids. The active agent may be released by diffusion as a result of a change in diffusivity of the stent body. The diffusivity of the active agent in the stent body may change as a result of polymer degradation and/or dissolution. Similar changes in the diffusivity of active agent in a coating on the stent body which includes a polymer may also occur. Other potential active release mechanisms are possible. In some embodiments the active agent will be released by any combination of the above mentioned mechanisms.

In some embodiments, the active agent may be incorporated into and/or coated onto the radiopaque metallic particles which are then mixed or dispersed within the polymer body. In those embodiments in which active agent is coated onto the radiopaque metallic particles, the surface of the radiopaque metallic particles may be entirely coated, or the surface may be partially coated, or there may be any combination of radiopaque metallic particles in which the surface is uncoated, entirely coated, and partially coated. In some embodiments of the invention in which the radiopaque metallic particles may be coated with the active agent, the coating may optionally include other materials such as, but not limited to, a polymer, binder, or carrier or any combination thereof. In addition to the above mentioned potential mechanisms for release of active agent, the active agent may be released when the radiopaque metallic particles are released, and/or the release of the active agent may occur concomitantly with, or after, the bioerosion of the radiopaque metallic particles. The active agent may be released by any of the methods outlined above with respect to the release from a stent body or coating. As an example of an embodiment in which the a coating of the radiopaque metallic particles include an active agent, the active agent may diffuse out of a coating on the metallic particles, and diffuse through the stent body to the bodily fluids or tissues, and/or may be released as a result of the degradation of the stent body.

In still other embodiments, the stent or device may be manufactured to be porous. Thus the stent or device could absorb active agent by soaking of the device in a solution or dispersion of the active agent with subsequent removal of the fluid or liquid. Another manner of filling the holes with a drug would be utilizing a vacuum.

In addition, in all embodiments mentioning "the active" or "an active," such embodiments encompass one active or a plurality of active agents which may release at the same rate, essentially the same rate, or at different rates. In addition, the plurality of active agents may be released by the same or different release mechanisms. The plurality of active agents may be incorporated in the body, in a stent coating, in or on the radiopaque metallic particles, or any combination thereof. As an example, in some embodiments one active agent may be incorporated in the stent body with one additional active agent incorporated in an exterior coating of the stent.

In any of the embodiments in which the stent further includes an active agent, the active agent may be released by any number of mechanisms, including but not limited to any one or any combination of the above mentioned release mechanisms, and in addition may be released by other mechanisms not specifically mentioned, but known in the art, such as, but not limited to, release due to osmotic effects.

Additional Materials

In some embodiments, the radiopaque stent body may be coated on the exterior. In some embodiments the exterior coating may include a radiopaque agent or a contrast agent. A contrast agent is a material comprising a radiopaque substance such as, but not limited to, Iodine. Some representative iodinated contrast agents may include, but are not limited to, acetriozate, diatriozate, iodimide, ioglicate, iothalamate, ioxithalamate, selectan, uroselectan, diodone, metrizoate, metrizamide, iohexol, ioxaglate, iodixanol, lipidial, ethiodol, and combinations thereof. Contrast agents also include biocompatible metallic salts such as Barium sulfate. In some embodiments radiopaque metallic particles may be included in the coating. In some embodiments the exterior coating may contain a polymer, and/or other additives, and may optionally include an active agent. In some embodiments the exterior coating may be devoid of contrast agent, radiopaque metallic particles, or any other radiopaque agent as well as devoid of active agent. The exterior coating may be applied for aesthetic reasons, to assist in insertion, and/or to enhance shelf-life stability or for any other reason.

In some embodiments, there may be more than one exterior coating layer, any of which may or may not contain active agent and/or may or may not contain any radiopaque agents which includes radiopaque metallic particles, and contrast agents. Thus in some embodiments one exterior coating may contain an active agent and one exterior coating may contain a radiopaque agent. In some embodiments, the radiopaque agent and/or radiopaque metallic particles, and the active agent may be included in one exterior coating. Some embodiments further include a second exterior coating containing neither active agent nor radiopaque substance. In some embodiments, a radiopaque agent or contrast agent may be included in at least one coating, and a plurality of active agents will be delivered with each active agent contained in a separate coating, while in some embodiments multiple active agents may be included in one coating, and optionally, multiple coatings containing multiple active agents may be applied. Variations of coatings with or without active agent and/or radiopaque agent, including radiopaque metallic particles, will be apparent to one of skill in the art, and all such variations or modifications are included in the scope of the present invention.

As outlined above, in some embodiments an adhesion promoter will be included in the stent body. Various adhesion promoters can be used for the surface modification of radiopaque metallic particles to improve adhesion between particles and polymer matrix. In one embodiment, an adhesion promoter can include a coupling agent. A coupling agent refers to a chemical substance capable of reacting with both the metallic particle and the polymer matrix of the composite material. A coupling agent acts as an interface between the polymer and the metallic particle to form a chemical bridge between the two to enhance the adhesion.

The adhesion promoter may include, but is not limited to, silane and non-silane coupling agents. For example, the adhesion promoter may include 3-aminopropyltrimethoxysilane, 3-aminopropyltriethoxysilane, aminopropylmethyldiethoxy silane, organotrialkoxysilanes, titanates, zirconates, and organic acid-chromium chloride coordination complexes. The chemical structure of a silane coupling agent can be described as Y—Si—(OR)$_3$. —OR stands for alkoxy groups, which can form strong chemical bonds with various radiopaque metallic particles, while Y— stands for organo-functional group, which can form strong physical or chemical bonds with a polymer matrix.

The particular coupling agent 3-aminopropyltrimethoxysilane has been used to enhance the bond between ceramic materials and bioabsorbable polymers, see for example, *Biomaterials*, 25 (2004) 2489-2500. The coupling agent 3-aminopropyltrimethoxysilane would be expected to enhance the bond between metallic particles and bioabsorbable polymers, see for example *BioMedical Engineering OnLine*, 2003, 2: 15. It is expected that the bond formed by the particular coupling agent 3-aminopropyltrimethoxysilane with metallic particles would become less strong in the presence of moisture. Thus, in some embodiments, 3-aminopropyltrimethoxysilane is used as a coupling agent to allow for degradation of the stent or device over time.

In particular, wetting agents may be needed to assure that each metallic particle is encapsulated or surrounded by polymer. One such wetting agent is maleic anhydride graft polyolefin resin (MA-g-PO). A specific example of a maleic anhydride graft polyloefin resin wetting agent is LICOMONT™ AR504 (Clariant GmbH) which is a chemically modified polypropylene which has been grafted with maleic anhydride to a high level of polarity. The physical and chemical properties of Licomont AR 504 are that it has a softening point at 156° C., an acid value of 41 mg KOH/g, a density of 91 g/cm$^3$, and a viscosity at 170° C. of 800 mPas. Another specific example of a wetting agent is LOTADER™ 8200 (Arkema, Inc.) a random terpolymer of ethylene, ethyl acrylate, and maleic anhydride. The physical and chemical properties of Lotader 8200 are 6.5% ethyl acrylate, 2.8% maleic anhydride, with a melt temperature of 100° C., a hardness shore D of 26 by ASTM D22640-85, a flexural modulus of 40 MPa per ASTM D790/ISO 178, a tensile strength at break of 8 MPa per ASTM D 638/ISO R527, and an elongation at break of 400% per ASTM D 638/ISO R527.

The choice of specific wetting agent will depend upon the type of polymer and type of metallic particles utilized. In particular, the type of polymer backbone for a graft-copolymer, or the monomers chosen for a copolymer of two or more monomer types, will differ for each type of polymer used. Exemplary polymers may include, but are not limited to, poly (L-lactic acid), poly (DL-lactic acid), poly(lactide-coglycolide). Therefore a wetting agent or adhesion promoter will be choosen such that one of more of the monomers which form poly (L-lactic acid), poly (DL-lactic acid), poly(lactide-coglycolide) is incorporated in a some sort of copolymer, and/or the backbone, or potentially the side chain, of a graft copolymer will include one of poly (L-lactic acid), poly (DL-lactic acid), poly(lactide-coglycolide). In some embodiments, the wetting agent or coupling agent will be chosen so that it is compatible with poly (L-lactic acid), poly (DL-lactic acid), poly(lactide-coglycolide). Other types of wetting agents which allow good contact between the metal and/or metallic particles, and the polymer and/or other materials may be used.

Anti-oxidants may be useful or beneficial. Some examples include IRGANANOX® B 225 and IRGANOX® 1010 (Ciba® Specialty Chemicals). Irganox B 225 is a combination of 50% IRGAFOS® 168 and 50% IRGANOX® 1010. It is believed that Irganox 1010 is the trade name for Tetrakis, or [methylene(3,5-di-t-butyl-4-hydroxyhydrocinnamate)] methane, and that the CAS number for Irganox 1010 is 6683-19-8. The chemical structure of Irgafos 168 is believed to be as follows:

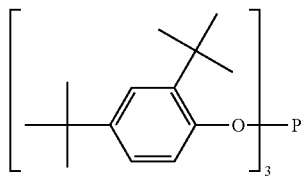

The chemical structure of Irganox 1010 is believed to be as follows:

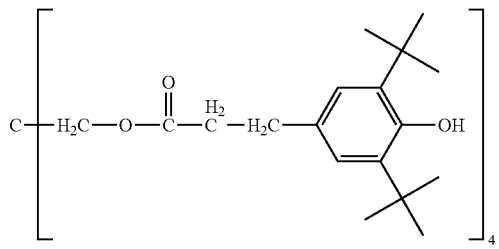

Other antioxidants compatible with polymers and the processing temperatures may be utilized. Other antioxidants include butylated hydroxyanisole (BHA), and butylated hydroxytoluene (BHT). Other commercial formulations include DURAND AX (Great Lakes Chemical), EHTANOX™ 310, an organotin catalyzed pentrythritol tetrakis (3-(3,5-di-t-butyl-4-hydroxyphenyl)propionate) and the tin free version, ETHANTOX™ 310 TF (Albemarle Corporation), and WESTCO™ SP 120 Styrenated Phenol, an antioxidant used for synthetic butyl rubber, CAS 61788-44-1, with mononsubstituted phenol 12-18%, disubstituted phenol 44-48%, trisubstituted phenol 34-42%, and phenol 1.0% maximum (Western Reserve Chemical, Stow, Ohio).

All embodiments may also includes additional components such as, but not limited to, wetting agents which enhance the surface wetting of the metallic particles (radiopaque or not), lubricating agents, fillers, plasticizing agents, surfactants, diluents, mold release agents, agents which act as active agent carriers or binders, anti-tack agents, anti-foaming agents, viscosity modifiers, anti-oxidants, potentially residual levels of solvents, and potentially any other agent which aids in, or is desirable in, the processing of the material, and/or is useful or desirable as a component of the final product. Other agents may be added which may be a variable in controlling the overall erosion rate of the stent.

How Manufactured

The stent may be manufactured by any number of processing techniques, but polymer processing techniques are particularly applicable. The stent may be manufactured from a tube or a sheet. The radiopaque metallic particles may be blended, mixed, or dispersed in the polymer and the dispersion or mixture then processed further to obtain a tube, sheet, or other form. The blending or dispersion may be done in an extruder, Banbury mixer (Ferdinand Rodriguez, *Principles of Polymer Systems Taylor and Francis*, Bristol Pa. 1996) or by use of other techniques known in the art. In particular, if the polymer is viscoelastic, techniques used in the rubber industry for the addition of carbon black to rubber (Rodriguez) may be applicable.

In blending the composite of polymer and radiopaque metallic particles, or polymer and metallic particles, care must be taken to prevent significant aggolmeration. This is particularly a problem with respect to smaller particles such as nano-particles. Additionally, obtaining a uniform dispersion by mixing particles with a polymer melt as described, is that particles can agglomerate or form clusters. The agglomeration of metallic particles makes it difficult to disperse the particles within the composite. The presence of larger clusters in the composite tends to result in a decrease in material performance. Such larger clusters can result in the formation of voids in a composite device, which are preferential sites for crack initiation and failure. The mechanical mixing in a conventional single screw extruder or in batch processing may be insufficient to break up the clusters, resulting in a non-uniform mixture of radiopaque metallic particles and polymer.

Various embodiments of forming a composite may be employed to increase the uniformity of dispersion of radiopaque metallic particles within a polymer in a composite. One set of embodiments may include forming a composite from a suspension of radiopaque metallic particles and a polymer solution. A composite formed using a suspension may result in a composite having more uniformly dispersed particles than the mixing methods described above.

Certain embodiments of a method of forming an implantable medical device may include forming a suspension including a fluid, a polymer, and radiopaque metallic particles. A "suspension" is a mixture in which particles are suspended or dispersed in a fluid. The fluid can be a solvent for the polymer so that the polymer is dissolved in the fluid. The particles can be mixed with the fluid before or after dissolving the polymer in the fluid. Various mechanical mixing methods known to those of skill in the art may be used to disperse the radiopaque particles in the suspension, including, but not limited to ultrasound, for example, by an ultrasonic mixer. The composite may then be formed from by evaporation of solvent.

In other embodiments, the polymer may be precipitated out of solution by the addition of a non-solvent for the polymer to the suspension which will precipitate the polymer, and may also precipitate out at least some of the radiopaque metallic particles. After the composite has been precipitated from the suspension, the residual solvent may be removed by heating, or exposure to a vacuum. It is believed that high polymer concentrations in solution, or in the suspension, lead to a higher percentage of the radiopaque metallic particles precipitating out with the polymer. Similarly, past a certain polymer concentration or viscosity of the suspension, the addition of more polymer leads to a decrease in the dispersion or distribution of the particles. Thus, the polymer concentration (or viscosity) for a given concentration of suspended radiopaque metallic particles.

A given suspension can have a particular combination of type of particles, particle concentration, and solvent. For this given suspension, the polymer weight percent or viscosity that can be varied to obtain both a desired degree of precipitation of particles and degree of dispersion of particles in the precipitated polymer. Thus, there may be a range of polymer weight percent or viscosity that can result in a desired degree of precipitation of particles and degree of dispersion of particles in precipitated polymer.

Additionally, it is believed that the manner of combining the suspension with the poor solvent can also affect the degree of precipitation and degree of dispersion. For example, depositing a fine mist of small droplets into a poor solvent can more readily result in a desired degree of precipitation and degree of dispersion. Thus, the manner of combining the suspension with the poor solvent can influence the range of polymer weight percent or viscosity that results in a desired degree of precipitation and degree of dispersion.

Exemplary polymers may include, but are not limited to, poly (L-lactic acid), poly (DL-lactic acid), and poly(lactide-coglycolide). Representative solvents for such polymers can include toluene and chloroform. Representative poor solvents for these polymers that may be used to precipitate the polymer include methanol, ethanol, isopropanol, and various alkanes such as hexane or heptane.

Another set of embodiments can include reducing the agglomeration of radiopaque metallic particles by decreasing the surface energy between particles to improve the dispersion of particles in the composite. The wetting agents and adhesion promoters outlined above may be particularly useful in some embodiments.

In still another set of embodiments, agglomeration can be reduced through mechanical mixing that applies shear stress to the particles sufficient to reduce the size of clusters of particles. Examples of mechanical means to reduce agglomeration include, but are not limited to, kneaders, compounders, or twin screw extruders.

In further embodiments, the composite formed from the suspension solution can be conveyed into an extruder. The composite mixture may be extruded at a temperature above the melting temperature of the polymer and less than the melting temperature of the radiopaque metallic particles. In some embodiments, the dried composite mixture may be broken into small pieces by, for example, chopping or grinding. Extruding smaller pieces of the composite mixture may lead to a more uniform distribution of the nano-particles, or radiopaque metallic particles, during the extrusion process.

In some other embodiments a form of geometric blending may be used. The metallic particles, and/or radiopaque metallic particles, may be preblended or compounded with a polymer at a high concentration, and then added to an extruder with additional polymer. The polymer used in the high volume preblended compound may be the same or a different polymer than that added to the extruder in a subsequent step.

The tube or sheet may be formed from a composite by any number of processes, including but not limited to, extrusion, injection molding, compression molding, and blow molding, and/or any combination thereof. The tube or sheet may be formed from the extruded composite mixture which has been broken into smaller pieces. Any of the polymer processing or blending techniques may involve the application of higher or lower temperatures or higher or lower pressures than ambient. The limitations in use of different temperatures and pressures will depend upon the properties of the polymers, the metallic particles, the existence of any active agent, and/or other variables.

The tube or sheet may be cut with a stent pattern by procedures known in the art such as, but not limited to, laser cutting or chemical etching. Examples of lasers that may be used for cutting stent patterns include, but are not limited to, excimer, $CO_2$, or YAG (yttrium aluminum garnet). In another embodiment, fibers may be formed from the polymer and radiopaque metallic particle mixture by techniques such as fiber spinning and formed into a stent. In the case of a sheet which is cut with a pattern, the tube may be joined together by welding or other techniques known in the art to form a tube. Other processes not specifically mentioned but known in the art may be used to manufacture the stent.

Coating of the exterior of the stent may be accomplished by procedures known in the art such as, but not limited to, painting, spraying, or dip coating. Coatings may be applied as a dry powder, or as an aqueous solution or solvent solution with subsequent removal of water and/or solvent. The coating may be applied by other procedures known in the art.

In some embodiments, the surface of the radiopaque metallic particles may be treated with an adhesion promoter prior to mixing with the polymer matrix. In one embodiment, the metallic particles can be treated with a solution containing the adhesion promoter. The treatment can include, but is not limited to, coating, dipping, or spraying the particles with an adhesion promoter or a solution including the adhesion promoter. The radiopaque metallic particles can also be treated with a gas containing the adhesion promoter. In one embodiment, treatment of the radiopaque metallic particles includes mixing the adhesion promoter with solution of distilled water and a solvent such as ethanol and then adding metallic particles. The radiopaque metallic particles can then be separated from the solution, for example, by a centrifuge, and the radiopaque particles can be dried. The radiopaque metallic particles may then be used to form a polymer composite. In an alternative embodiment, the adhesion promoter can be added to the particles during formation of the composite. For example, the adhesion promoter can be mixed or dispersed with a radiopaque metallic/polymer mixture or dispersion during extrusion.

How Used

Stents are often used in the treatment of atherosclerotic stenosis in blood vessels. However, stents have a number of other uses, also outlined above.

In the typical method of using a stent, the first step in treatment of a diseased site with a stent is locating a region that may require treatment such as a suspected lesion in a vessel, typically by obtaining an X-ray image of the vessel. One means of obtaining an image is injecting a contrast agent, which contains a radiopaque substance such as iodine into a vessel. The x-ray image depicts the lumen of the vessel from which a physician can identify a potential treatment region. The treatment then involves both delivery and deployment of the stent. Delivery and deployment of a stent are often accomplished by positioning the stent about one end of a catheter, inserting the end of the catheter through the skin into a bodily lumen, advancing the catheter in the bodily lumen to a desired treatment location, expanding the stent at the treatment location, and removing the catheter from the lumen. In the case of a balloon expandable stent, the stent is mounted about a balloon disposed on the catheter. Mounting the stent typically involves compressing or crimping the stent onto the balloon. The stent is then expanded by inflating the balloon. The balloon may then be deflated and the catheter withdrawn. In the case of a self-expanding stent, the stent may be secured to the catheter via a retractable sheath or a sock. When the stent is in a desired bodily location, the sheath may be withdrawn allowing the stent to self-expand.

Real time visualization of the delivery of the stent is desirable for accurate stent placement, and thus the radiopacity of the embodiments of the stents of the present invention allow for accurate placement of the stent at a treatment site. A cardiologist or interventional radiologist can track the delivery catheter through the patient's vasculature and precisely place the stent at the site of a lesion. This is typically accomplished by fluoroscopy or similar x-ray visualization procedures. In addition, some embodiments of the present invention will allow for visualization of the stent for some time period after deployment.

Stents, including embodiments of the present invention, may be delivered and deployed by other techniques known in the art.

Detailed List of Potential Material

Representative examples of radiopaque metals that may be used to fabricate radiopaque particles for the various embodiments of the stents of the present invention include, but are not limited to Iridium (Ir), Platinum (Pt), Gold (Au), Silver (Ag), Ruthenium (Ru), Rhenium (Re), Osmium (Os), Tungsten (W), Palladium (Pd), Rhenium (Rh), Tantalum (Ta), Hafnium (Hf), Molybdenum (Mo), Iron (Fe), Zinc (Zn), and Magnesium (Mg), Aluminum (Al), Titanium (Ti), Nickel (Ni), Niobium (Nb), Zirconium (Zr), Copper (Cu), and Tin (Sn). In addition, various alloys can be used, such as but not limited to, Magnesium/Zinc, Magnesium/Iron, Zinc/Iron, and Magnesium/Zinc/Iron. Representative metals that may be used to fabricate radiopaque particles for the various embodiments of the present invention, and that may be bioerodible or self-dissolving, include, but are not limited to, Magnesium (Mg), Manganese (Mn), Potassium (K), Calcium (Ca), Sodium (Na), Zinc (Zn), Chromium (Cr), Iron (Fe), Cadmium (Cd), Aluminum (Al), Cobalt (Co), Antimony (Sb), Tin (Sn), Vanadium (V), Copper (Cu), Molybdenum (Mo) and Tungsten (W).

Representative examples of polymers that may be used to fabricate embodiments of stents and coatings for stents of the present invention include, but are not limited to, poly(N-acetylglucosamine) (Chitin), Chitosan, poly(3-hydroxyvalerate), poly(lactide-co-glycolide), poly(3-hydroxybutyrate), poly(4-hydroxybutyrate), poly(3-hydroxybutyrate-co-3-hydroxyvalerate), polyorthoesters, polyanhydride, poly(glycolic acid), poly(glycolide), poly(L-lactic acid), poly(L-lactide), poly(D,L-lactic acid), poly(D,L-lactide), poly(L-lactide-co-D,L-lactide), poly(caprolactone), poly(L-lactide-co-caprolactone), poly(D,L-lactide-co-caprolactone), poly (glycolide-co-caprolactone), poly(trimethylene carbonate), polyester amide, poly(glycolic acid-co-trimethylene carbonate), co-poly(ether-esters) (e.g. PEO/PLA), polyphosphazenes, biomolecules (such as fibrin, fibrinogen, cellulose, starch, collagen, and hyaluronic acid), polyurethanes, silicones, polyesters, polyolefins, polyisobutylene and ethylene-alphaolefin copolymers, acrylic polymers and copolymers, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates, polyoxymethylenes, polyimides, polyethers, polyurethanes, rayon, rayon-triacetate, cellulose acetate, cellulose butyrate, cellulose acetate butyrate, cellophane, cellulose nitrate, cellulose propionate, cellulose ethers, and carboxymethyl cellulose, and combinations thereof.

Additional representative examples of polymers that may be especially well suited for use in fabricating embodiments of implantable medical devices disclosed herein include ethylene vinyl alcohol copolymer (commonly known by the generic name EVOH or by the trade name EVAL), poly(butyl methacrylate), poly(vinylidene fluoride-co-hexafluoropropene) (e.g., SOLEF 21508, available from Solvay Solexis PVDF, Thorofare, N.J.), polyvinylidene fluoride (otherwise known as KYNAR, available from ATOFINA Chemicals, Philadelphia, Pa.), ethylene-vinyl acetate copolymers, poly(vinyl acetate), styrene-isobutylene-styrene triblock copolymers, and polyethylene glycol. Additional representative examples of polymers that may be particularly well suited for use in fabricating embodiments of implantable medical devices disclosed herein is Poly(L-lactide).

Any copolymer, whether random, graft, or block copolymers, including any one or more of the polymers in the above list (and/or constituent monomers of the polymers in the above list), regardless of which other polymer, polymers, or monomers comprise the copolymer, and without regard for whether or not the other polymer, polymers or monomers are specifically listed herein, is also encompassed in the current invention. Various embodiments of the current invention encompass both uncross-linked and cross-linked polymers.

Drugs or therapeutic active agent(s) can include anti-inflammatories, antiproliferatives, and other bioactive agents.

An antiproliferative agent can be a natural proteineous agent such as a cytotoxin or a synthetic molecule. Preferably, the active agents include antiproliferative substances such as actinomycin D, or derivatives and analogs thereof (manufactured by Sigma-Aldrich 1001 West Saint Paul Avenue, Milwaukee, Wis. 53233; or COSMEGEN available from Merck) (synonyms of actinomycin D include dactinomycin, actinomycin IV, actinomycin $I_1$, actinomycin $X_1$, and actinomycin $C_1$), all taxoids such as taxols, docetaxel, and paclitaxel, paclitaxel derivatives, all olimus drugs such as macrolide antibiotics, rapamycin, everolimus, structural derivatives and functional analogues of rapamycin, structural derivatives and functional analogues of everolimus, FKBP-12 mediated mTOR inhibitors, biolimus, perfenidone, prodrugs thereof, co-drugs thereof, and combinations thereof. Representative rapamycin derivatives, include 40-O-(3-hydroxy)propyl-rapamycin, 40-O-[2-(2-hydroxy)ethoxy]ethyl-rapamycin, or 40-O-tetrazole-rapamycin, 40-epi-(N1-tetrazolyl)-rapamycin (ABT-578 manufactured by Abbot Laboratories, Abbot Park, Ill.), prodrugs thereof, co-drugs thereof, and combinations thereof. In one embodiment, the anti-proliferative agent is everolimus.

An anti-inflammatory drug can be a steroidal anti-inflammatory agent, a nonsteroidal anti-inflammatory agent, or a combination thereof. In some embodiments, anti-inflammatory drugs include, but are not limited to, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, ciclofen, cintazone, cliprofen, clobetasol propionate, clobetasone butyrate, clopirac, cloticasone propionate, cormethasone acetate, cortodoxone, deflazacort, desonide, desoximetasone, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, methylprednisolone suleptanate, momiflumate, nabumetone, naproxen, naproxen sodium, naproxol, nimazone, olsalazine sodium, orgotein, orpanoxin, oxaprozin, oxyphenbutazone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, sudoxicam, sulindac, suprofen, talmetacin, talniflumate, talosalate, tebufelone, tenidap, tenidap sodium, tenoxicam, tesicam, tesimide, tetrydamine, tiopinac, tixocortol pivalate, tolmetin, tolmetin sodium, triclonide, triflumidate, zidometacin, zomepirac sodium, aspirin (acetylsalicylic acid), salicylic acid, corticosteroids, glucocorticoids, tacrolimus, pimecorlimus, prodrugs thereof, co-drugs thereof, and combinations thereof. In one embodiment, the anti-inflammatory agent is clobetasol.

Alternatively, the anti-inflammatory may be a biological inhibitor of proinflammatory signaling molecules. Anti-inflammatory biological agents include antibodies to such biological inflammatory signaling molecules.

In addition, drugs or active can be other than antiproliferative agents or anti-inflammatory agents. These active agents can be any agent which is a therapeutic, prophylactic, or a diagnostic agent. In some embodiments, such agents may be used in combination with antiproliferative or anti-inflammatory agents. These agents can also have anti-proliferative and/or anti-inflammatory properties or can have other properties such as antineoplastic, antiplatelet, anti-coagulant, anti-fibrin, antithrombonic, antimitotic, antibiotic, antiallergic, antioxidant, and cystostatic agents. Examples of suitable therapeutic and prophylactic agents include synthetic inorganic and organic compounds, proteins and peptides, polysaccharides and other sugars, lipids, and DNA and RNA nucleic acid sequences having therapeutic, prophylactic or diagnostic activities. Nucleic acid sequences include genes, antisense molecules which bind to complementary DNA to inhibit transcription, and ribozymes. Some other examples of other bioactive agents include antibodies, receptor ligands, enzymes, adhesion peptides, blood clotting factors, inhibitors or clot dissolving agents such as streptokinase and tissue plasminogen activator, antigens for immunization, hormones and growth factors, oligonucleotides such as antisense oligonucleotides and ribozymes and retroviral vectors for use in gene therapy. Examples of antineoplastics and/or antimitotics include methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, thrombin inhibitors such as Angiomax ä (Biogen, Inc., Cambridge, Mass.), calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), nitric oxide or nitric oxide donors, super oxide dismutases, super oxide dismutase mimetic, 4-amino-2,2,6,6-tetramethylpiperidine-1-oxyl (4-amino-TEMPO), estradiol, anticancer agents, dietary supplements such as various vitamins, and a combination thereof. Examples of such cytostatic substance include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.). An example of an antiallergic agent is permirolast potassium. Other therapeutic substances or agents which may be appropriate include alpha-interferon, and genetically engineered epithelial cells. The foregoing substances are listed by way of example and are not meant to be limiting.

Other bioactive agents may include antiinfectives such as antiviral agents; analgesics and analgesic combinations; anorexics; antihelmintics; antiarthritics, antiasthmatic agents; anticonvulsants; antidepressants; antidiuretic agents; antidiarrheals; antihistamines; antimigrain preparations; antinauseants; antiparkinsonism drugs; antipruritics; antipsychotics; antipyretics; antispasmodics; anticholinergics; sympathomimetics; xanthine derivatives; cardiovascular preparations including calcium channel blockers and beta-blockers such as pindolol and antiarrhythmics; antihypertensives; diuretics; vasodilators including general coronary; peripheral and cerebral; central nervous system stimulants; cough and cold preparations, including decongestants; hypnotics; immunosuppressives; muscle relaxants; parasympatholytics; psychostimulants; sedatives; tranquilizers; naturally derived or genetically engineered lipoproteins; and restenoic reducing agents. Other active agents which are currently available or that may be developed in the future are equally applicable.

EXAMPLES

The examples set forth below are for illustrative purposes only and are in no way meant to limit the invention. The following examples are given to aid in understanding the invention, but it is to be understood that the invention is not limited to the particular materials or procedures of examples.

Example 1

Manufacture and Visualization of Radiopaque Stents

Poly(L-lactide) (PLLA) and Tungsten were blended together in a single screw extruder to produce composite polymer-metallic tubing. The tubing was expanded in a blow molder. A stent pattern was cut into the tubing with a femtosecond laser. The stents were then tested for radiopacity using a fluoroscope. Two levels of Tungsten were investigated, 5% and 10% by volume (nominal theoretical volume) of Tungsten, blended with the PLLA. The theoretical % volume is obtained by the following equation: volume % tungsten=100*{(mass of Tungsten/density of Tungsten)/[(mass of Tungsten/density of Tungsten)+(mass of polymer/density of polymer)]} where "*" represents multiplication. Thus, the 5% and 10% by volume investigated here are based on a theoretical volume percent, and the calculations do not take into account any change in volume upon blending.

In addition, for the proof of concept experiment presented here, the Tungsten added was not pure, or substantially pure, Tungsten. The source of Tungsten was a high volume percent Tungsten blended with a polyether block polyamide copolymer (PEBAX® from Arkema, Inc.) with a Shore durometer of about 40 D. Pebax is a polyether block polyamide copolymer of the general formula:

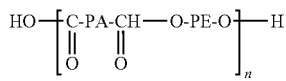

where "PA" represents polyamide and "PE" represents polyether sections, and n is the number of repeat units. The polyamide is a rigid section and the polyether is a flexible section. In this case the weight percent Tungsten was approximately 92 percent, with the balance being the PEBAX 40 D and additives of wetting agent, Licomont AR504, and anti-oxidant, Irganox B225, as outlined below. Tungsten particle size was within a particle size distribution having an average particle size range of at least 2 microns to 10 microns and a maximum particle size of about 20 microns.

The compositions and process for the manufacture of the composite high volume percent Tungsten compound is outlined in paragraph 29 of US patent application publication, 2005/0064224 A1, which essentially follows. The composite used in Example 1 of the present invention for the proof of concept experiment is preferably made by first blending the polymer resin and wetting agent, and optionally, an antioxidant such as by tumble mixing after which such blend is introduced into a twin-screw extruder via a primary feeder. The feed rate is carefully controlled in terms of mass flow rate to ensure that a precise fill ratio is achieved upon subsequent combination with the radiopaque agent. The heat that the materials are subjected as they are conveyed through the extruder causes the polymer to melt to thereby facilitate thorough homogenization of all of the ingredients. The radiopaque agent powder, selected for its uniform particle shape and controlled particle size distribution, as described above, is subsequently introduced into the melt stream via a secondary feeder, again at a carefully controlled mass flow rate so as to achieve the target fill ratio. The solid powder, molten polymer and additives are homogenized as they are conveyed downstream and discharged through a die as molten strands which are cooled in water and subsequently pelletized. The preferred extrusion equipment employs two independent feeders as introduction of all components through a single primary feeder would require significantly higher machine torques and result in excessive screw and barrel wear. The powder feeder is preferentially operated in tandem with a sidefeeder device, which in turn conveys the powder through a sealed main barrel port directly into the melt stream. A preferred composition comprises a fill ratio of at least 90.8 weight percent of Tungsten (H. C. Starck's Kulite™ HC600s, HC180s and KMP-103JP) to Pebax® 10D. A maleic anhydride source in the form of Licomont® AR504 is initially added to the polymer resin at the rate of approximately 3 pphr while an antioxidant in the form of Ciba Geigy Irganox®

B225 at the rate of approximately 2 pphr (parts per hundred relative to the resin). The temperature to which materials are subjected to in the extruder is about 221° C.

In the example here, the Pebax/tungsten/Irganox B225/Licomont AR504 compounded blend, or composite, was not added for purposes of radiopacity, but the composite was used as a convenient source of Tungsten. The wetting agent, and likely the antioxidant, would have been included in a blend or composite, even in the absense of Pebax. As outlined above a coupling agent or other adhesion promoter may be desirable in the final composition and may be used in addition to or instead of the wetting agent.

Also, the values of 5% and 10% volume percent are "nominal" since the experiments effectively ignored the difference between the density of the Pebax polymer and PLLA polymer. In other words, the mass of Tungsten-polymer extrusion was assumed to be 92% by weight Tungsten, and 8% by weight polymer, but the theoretical % volume of the polymer utilized the density of PLLA to estimate the volume occupied by both the PLLA polymer and the Pebax polymer. In other words, the theoretical volume %=((mass of Tungsten compound*weight fraction Tungsten)/density of Tungsten)/[((mass of Tungsten compound*weight fraction Tungsten)/density of Tungsten)+({(mass of PLLA polymer)+(mass of compound*weight fraction of Pebax polymer)}/density of PLLA polymer)]. The theoretical volume percent of Tungsten is actually slightly different than the 5% and 10% reported here. Although the blends will be referred to as 5% and 10%, these number represent only the nominal values.

Figure 2:
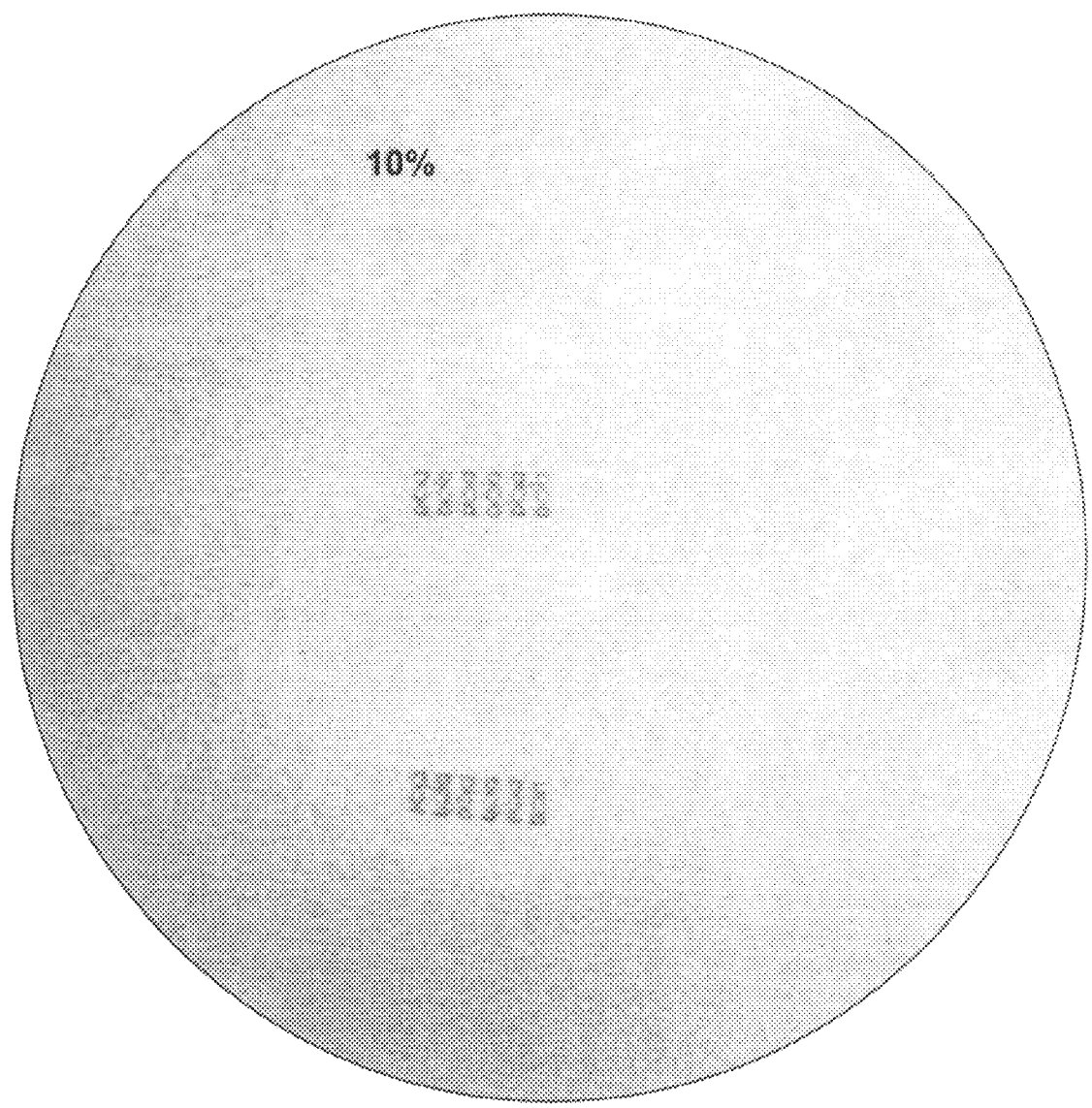
FIG. 2 depicts a fluoroscopic image of an embodiment of the present invention, that is a stent including 10% Tungsten in the polymer poly(L-lactide) as manufactured.
Figure 3:
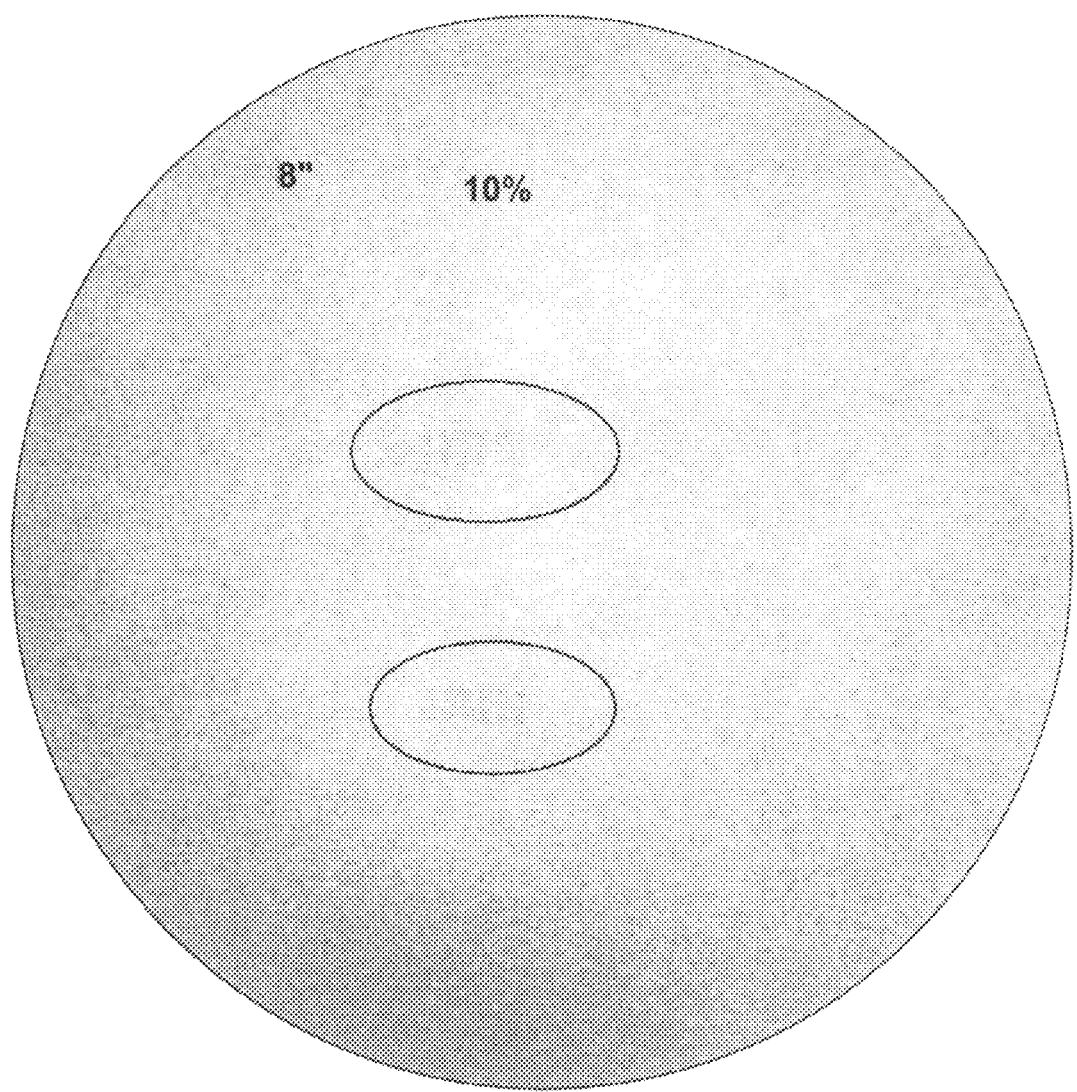
FIG. 3 depicts a fluoroscopic image of an embodiment of the present invention, that is a stent including 10% Tungsten in the polymer poly(L-lactide) on top of acrylic plastic.
Figure 4:
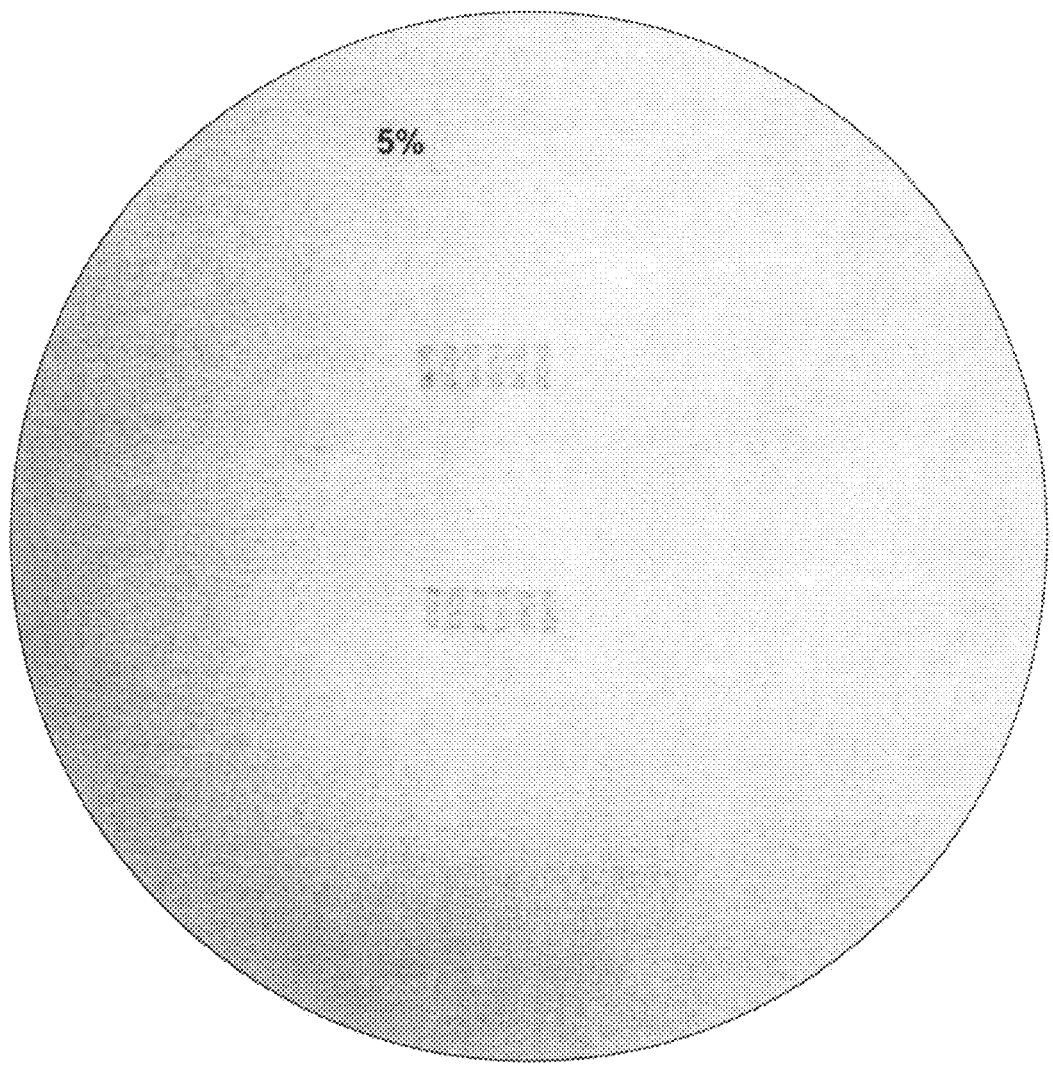
FIG. 4 depicts a fluoroscopic image of an embodiment of the present invention, that is a stent including 5% Tungsten in the polymer poly(L-lactide) as manufactured.
Figure 5:
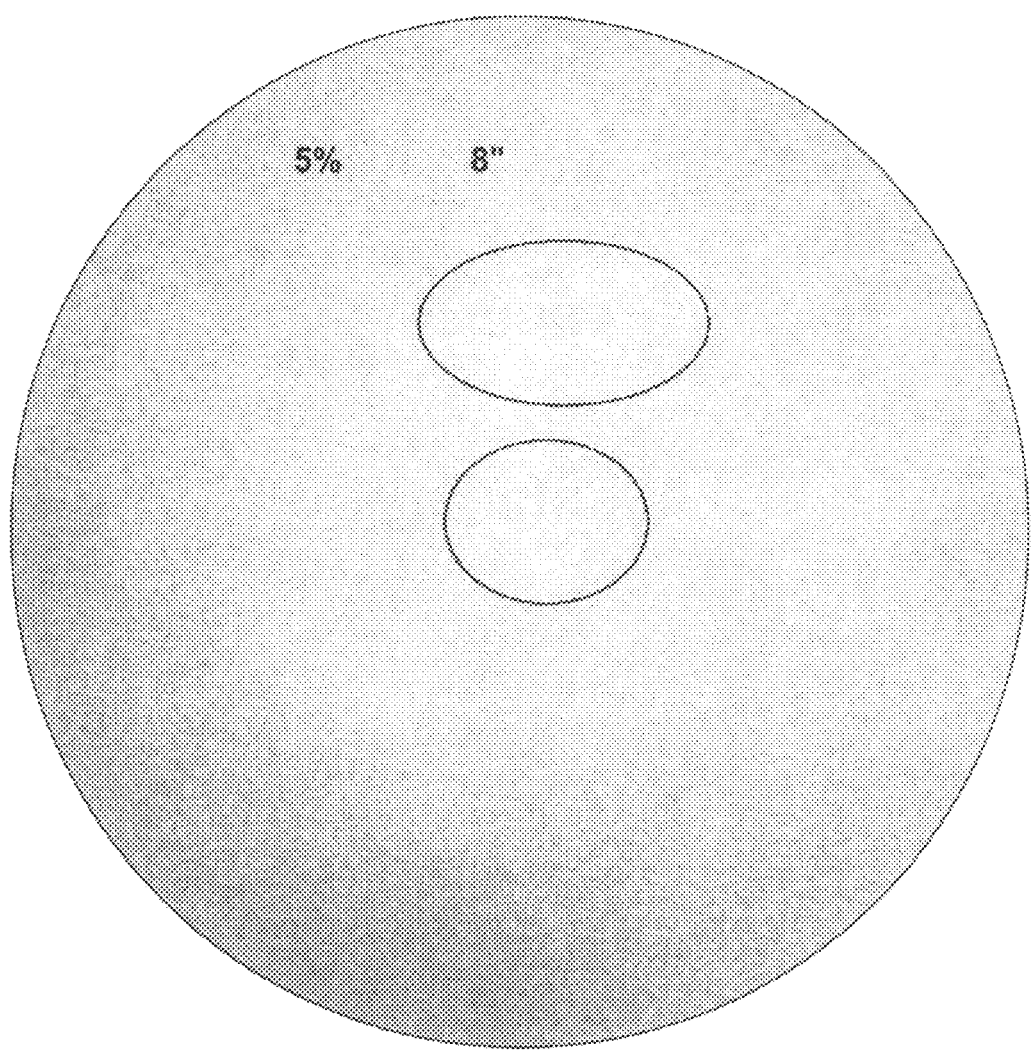
FIG. 5 depicts a fluoroscopic image of an embodiment of the present invention, that is a stent including 5% Tungsten in the polymer poly(L-lactide) on top of acrylic plastic.

FIGS. 2 and 3 are fluoroscopic images of the stents manufactured with 10% by volume of Tungsten. FIG. 2 is a fluoroscopic image of the stents as manufactured while FIG. 3 is a fluoroscopic image of the stents placed on top of an eight inch thick layer of acrylic plastic. The acrylic plastic is intended to approximate the intensity loss that would occur if the stent were implanted in an obese person. Although the stent is placed on top of the acrylic plastic, the X-rays penetrate both objections before detection, and the acrylic plastic attenuates the signal from the radiopaque stent. Similarly FIGS. 4 and 5 are fluoroscopic images of the stents manufactured with 5% by volume of Tungsten where FIG. 4 is the fluoroscopic image of the as manufactured stents, and the FIG. 5 is the fluoroscopic image of the stents placed on top of an eight inch thick sheet of acrylic plastic. In FIGS. 3 and 5, elliptical shapes have been added to the digitized image using a computer software to highlight the location of the stent. As shown in FIGS. 3 and 5, there is some attenuation of the image due to the acrylic plastic.

Example 2

Prospective Example of Surface Modification of Radiopaque Metallic Particles

This prospective example illustrates how the surface of the radiopaque metallic particles may be modified to enhance adhesion between the particles and the polymer of which the stent body is fabricated.

As discussed above, the mechanical properties of a polymer/metallic particle composite can be improved by enhancing the interfacial adhesion. The adhesion between metallic particles and a biodegradable polymer can be improved by coating at least a portion of the surfaces of the metallic particles with an adhesion promoter such as 3-aminopropyltrimethoxysilane and 3-aminopropyltriethoxysilane.

Step 1: Add 50 ml distilled water to 950 ml Ethanol and stir for 15-30 minutes.

Step 2: Add 10 g 3-aminopropyltrimethoxysilane to water-ethanol mixture and stir for 1 hour.

Step 3: Add 10 g radiopaque metallic particles and stir for 2 hours.

Step 4: Centrifuge the radiopaque metallic particles modified from solution.

Step 5: Dry radiopaque metallic particles in a vacuum oven at 70° C. until the constant weight.

Example 3

Prospective Example of Stent Fabrication from the Composite of Polymer and Surface Modified Radiopaque Metallic Particles This prospective example illustrates how the surface modified radiopaque metallic particles may be used in the fabrication of a stent.

Step 1: The composite of PLLA and surfaced modified radiopaque metallic particles is prepared through compounding using a twin screw extruder.

Step 2: A tubing of PLLA/metal particle composite is obtained through the extrusion of the composite formed in step 1 using a signal screw extruder.

Step 3: The tubing is expanded at 100° C. in a blow molder to further increase its radial strength.

Step 4: A stent pattern is cut in the expanded tubing using an ultra-fast pulse laser.

Step 5: The stent is crimped at 30° C. After crimping, the stent is sterilized with electron beam radiation at a temperature less than ambient.

The above examples and disclosure are intended to be illustrative and not exhaustive. These examples and description will suggest many variations and alternatives to one of ordinary skill in this art. All such alternatives and variations are intended to be included where the term "comprising" means "including, but not limited to".

What is claimed is:
1. A stent comprising:
   a scaffolding comprising
      a polymer; and
      radiopaque metallic particles mixed or dispersed within the polymer;
   wherein the stent is self-expanding or balloon-expandable;
   wherein the stent is visible in an X-ray image;
   wherein the radiopaque metallic particles comprise a galvanic couple to facilitate corrosion of the radiopaque metallic particles; and
   wherein the radiopaque metallic particles comprise an alloy comprising Tungsten.
2. The stent of claim 1, wherein the radiopaque metallic particles comprise bioerodible metallic particles.
3. The stent of claim 1, wherein the polymer comprises a biostable polymer.
4. The stent of claim 1, wherein the polymer comprises a biodegradable polymer.
5. The stent of claim 1, wherein the radiopaque metallic particles comprise nano-particles.
6. The stent of claim 1, wherein the stent scaffolding further comprises an active agent.
7. The stent of claim 1, further comprising a coating on at least a portion of a surface of the scaffolding, the coating being a discrete layer, and the coating comprising an active agent.
8. The stent of claim 1, further comprising a coating on at least a portion of a surface of the scaffolding;

wherein the coating is a discrete layer, and the coating comprises a radiopaque agent.

9. The stent of claim 1, wherein the radiopaque metallic particles comprise about 2% to about 36% by volume of the stent scaffolding.

10. The stent of claim 1, wherein the radiopaque metallic particles comprise about 5% to about 30% by volume of the stent scaffolding.

11. The stent of claim 1, wherein the radiopaque metallic particles further comprise an adhesion promoter that enhances adhesion of the radiopaque metallic particles with the polymer.

12. The stent of claim 11, wherein the adhesion promoter comprises a coupling agent.

13. The stent of claim 12, wherein the coupling agent comprises a silane coupling agent.

14. The stent of claim 11, wherein the adhesion promoter is selected from the group consisting of 3-aminopropyltrimethoxysilane, 3-aminopropyl-triethoxysilane, aminopropylmethyldiethoxy silane, and combinations thereof.

15. The stent of claim 1, wherein the radiopaque metallic particles are substantially uniformly or uniformly distributed within the polymer.

16. The stent of claim 1, wherein the stent scaffolding is bioerodible.

17. The stent of claim 1, wherein the stent scaffolding comprises sufficient radiopacity to be imaged by X-Ray radiation throughout all or most of the useful life of the stent.

18. The stent of claim 1, wherein the stent scaffolding is designed to be crimped to a smaller diameter for delivery to a treatment site in a patient and expanded upon deployment at the treatment site in the patient.

19. The stent of claim 1, wherein the stent scaffolding comprises a network of interconnecting structural elements.

20. The stent of claim 1, wherein the stent scaffolding comprises a coil.

21. The stent of claim 1, wherein the scaffolding of the stent provides all, or substantially all, of the structural support for the stent.

22. A stent comprising:
a scaffolding comprising
    a polymer; and
    radiopaque metallic particles mixed or dispersed within the polymer;
and the stent further comprising a coating on at least a portion of a surface of the scaffolding, the coating being a discrete layer, and the coating comprising a radiopaque agent;
wherein the stent is self-expanding or balloon-expandable;
wherein the stent is visible in an X-ray image; and
wherein the radiopaque metallic particles comprise a galvanic couple to facilitate corrosion of the radiopaque metallic particles.

23. A stent comprising:
a scaffolding comprising
    a polymer; and
    radiopaque metallic particles mixed or dispersed within the polymer;
wherein the stent is self-expanding or balloon-expandable;
wherein the stent is visible in an X-ray image;
wherein the radiopaque metallic particles comprise a galvanic couple to facilitate corrosion of the radiopaque metallic particles; and
wherein the radiopaque metallic particles are greater than 20 microns in size.

* * * * *